(12) United States Patent
Trcek

(10) Patent No.: US 10,196,601 B2
(45) Date of Patent: Feb. 5, 2019

(54) CELL CULTURE MEDIUM AND PROCESS FOR CONTROLLING α-AMIDATION AND/OR C-TERMINAL AMINO ACID CLEAVAGE OF POLYPEPTIDES

(71) Applicant: LEK PHARMACEUTICALS D.D., Ljubljana (SI)

(72) Inventor: Tanja Ficko Trcek, Ljubljana (SI)

(73) Assignee: LEK PHARMACEUTICALS D.D., Ljubljana (SK)

( * ) Notice: Subject to any disclaimer, the term of this patent is extended or adjusted under 35 U.S.C. 154(b) by 0 days.

(21) Appl. No.: 14/913,312

(22) PCT Filed: Aug. 20, 2014

(86) PCT No.: PCT/EP2014/067762
§ 371 (c)(1),
(2) Date: Feb. 19, 2016

(87) PCT Pub. No.: WO2015/024977
PCT Pub. Date: Feb. 26, 2015

(65) Prior Publication Data
US 2016/0201028 A1     Jul. 14, 2016

(30) Foreign Application Priority Data

Aug. 20, 2013 (EP) .................................... 13181027

(51) Int. Cl.
*C12N 5/00* (2006.01)
*C07K 16/24* (2006.01)

(52) U.S. Cl.
CPC .......... *C12N 5/0018* (2013.01); *C07K 16/241* (2013.01); *C12N 2500/05* (2013.01); *C12N 2500/20* (2013.01); *C12N 2500/22* (2013.01)

(58) Field of Classification Search
CPC .............. C07K 16/241; C12N 2500/05; C12N 2500/20; C12N 2500/22; C12N 5/0018
See application file for complete search history.

(56) References Cited

U.S. PATENT DOCUMENTS

| 5,723,765 | A | 3/1998 | Oliver et al. | |
|---|---|---|---|---|
| 9,181,572 | B2 * | 11/2015 | Subramanian | C12P 21/00 |
| 2008/0305523 | A1 | 12/2008 | Wenzel et al. | |
| 2011/0117643 | A1 | 5/2011 | Kim et al. | |
| 2013/0034897 | A1 | 2/2013 | Mehta et al. | |
| 2013/0158273 | A1 | 6/2013 | Kadaboina et al. | |
| 2014/0273092 | A1 | 9/2014 | Flikweert et al. | |

FOREIGN PATENT DOCUMENTS

| EP | 0148605 A2 | 7/1985 |
|---|---|---|
| EP | 0409294 A1 | 1/1991 |
| EP | 1050582 A2 | 11/2000 |
| EP | 2560479 A2 | 2/2013 |
| GB | 2220938 A | 1/1990 |
| GB | 2233978 A | 1/1991 |
| JP | 2010519909 A | 6/2010 |
| WO | WO-91/09955 A1 | 7/1991 |
| WO | WO-93/09222 A2 | 5/1993 |
| WO | WO-2006/004728 A2 | 1/2006 |
| WO | WO-2008/109410 A1 | 9/2008 |
| WO | WO-2009/149719 A1 | 12/2009 |
| WO | WO-2011/134920 A1 | 11/2011 |
| WO | WO-2012/062810 A2 | 5/2012 |
| WO | WO-2013/156458 A1 | 10/2013 |
| WO | PCT/EP14/067762 | 8/2014 |

OTHER PUBLICATIONS

"Selenium in Cell Culture: Sigma-Aldrich", (2014), Retrieved from the Internet: http://www.sigmaaldrich.com/life-sciencejcell-culturejlearning-centerjmedia-expertjselenium.html (2 pages).
Bradbury, et al. (1989) "4-Phenyl-3-butenoic acid, an in vivo inhibitor of peptidylglycine hydroxylase (peptide amidating enzyme)", European Journal of Biochemistry; 189: 363-368.
Cao, et al, "Potent and selective inhibitors of human peptidylglycine [alpha]-amidating monooxygenase", MedChemComm., vol. 2, No. 8, (2011) (4 pages).
Eipper, et al., (1991) "Peptidyl-alpha-hydroxyglycine alpha-amidatinglyase: Purification, characterization, and expression", The Journal of Biological Chemistry. 266: 7827-7833.
Kim, et al., (2001) "Peptide Amidation: Production of Peptide Hormones in vivo and in vitro", Biotechnology and Bioprocess Engineering; 6: 244-251.
Kovar, "Hybridoma Cultivation in Defined Serum-Free Media: Growth-Supportig Substances v. Trace Elements", Folia Biologica, vol. 34, No. 1, (1988), pp. 35-41).
Liu, et al., "Heterogeneity of Monoclonal Antibodies", Journal of Pharmaceutical Sciences; 97: 2426-2447.
Manillère, et al., (1995) "Fine chemical modifications at N- and C-termini enhance peptide presentation to T cells by increasing the lifespan of both free and MHC-complexed peptides", Molecular Immunology; 32:1377-1385.
Marakova, et al., "The Zn-peptidase superfamily: functional convergence after evolutionary divergence", J. Mol. Bio., vol. 292, No. 1, (1999) (pp. 11-17).
May, et al., "Regulation of peptide amidation in cultured pituitary cells.", J. Bio. Chem., vol. 260, No. 30, (1985) (pp. 16224-16231).
Merkler DJ. (1994) "C-terminal amidated peptides: production by the in vitro enzymatic amidation of glycine-extended peptides and the importance of the amide to bioactivity", Enzyme and Microbial Technology; 16: 450-456.
Metha, et al., (2009) "C Teriminal a-Amidation. In: Walsh G. Post translational modification of Protein biopharmacetuticals", Wiley-VCH Verlag GmbH, Co.KGaA, Weinheim, Germany, pp. 253-276.
www Features.BioTechniques.com, (2011) Retrieved from the Internet:http://www.biotechniques.com/multimediajarchive/00147/BTN A 000113666 0 147009a.pdf (6 pages).

(Continued)

Primary Examiner — Delia M Ramirez
(74) Attorney, Agent, or Firm — Ballard Spahr LLP

(57) ABSTRACT

The present invention is related to a cell culture medium for reducing the C-terminal heterogeneity of a polypeptide expressed in cell-culture, wherein the medium comprises at least one essential trace element in an effective amount, and to a cell culture process for reducing C-terminal heterogeneity of a protein, in which process an essential trace element is used.

9 Claims, 14 Drawing Sheets

(56) References Cited

OTHER PUBLICATIONS

Zhang, et al., "A novel function for selenium in biological system: selenite as a highly effective iron carrier for Chinese hamster ovary cell growth and monoclonal antibody production", Biotech. and Enginr., vol. 95, No. 6, (2006) pp. 1188-1197.
International Search Report and Written Opinion of the International Searching Authority dated Nov. 19, 2014 for application PCT/EP2014/067762, filed on Aug. 20, 2014 and published as WO 2015/024977 on Feb. 26, 2015 (Applicant—LEK Pharma., D.D. // Inventor—Ficko Trcek) (23 pages).
Partial European Search Report dated Jan. 29, 2014 for application EP 13181027.7 (Applicant—LEK Pharma., D.D. // Inventor—Ficko Trcek) (8 pages).
Karlenius, T. C. et al., The selenium content of the cell culture serum influences redox—regulated gene expression, Biotechniques., (2011), vol. 50, No. 5, pp. 295-301.
Kovar, Hybridoma Cultivation in Defined Serum-free Media: Growth-supporting Substances V. Trace Elements, Folia Biologica (Praha), (1998), vol. 34, No. 1, pp. 35-41.
Makarova et al., The Zn-peptidase Superfamily: Functional Convergence After Evolutionary Divergence, Journal of Molecular Biology, (1999), vol. 292, No. 1, pp. 11-17.
May, V. et al, Regulation of peptide Amidation in Cultured Pituitary Cells, J Biol. Chem. (1985);260(30):16224-31.
Zhang et al, A Novel Function for Selenium in Biological System: Selenite as a Highly Effective Iron Carrier for Chinese Hamster Ovary Cell Growth and Monoclonal Antibody Production, Biotechnology and Bioengineering, (2006), vol. 95, No. 6, pp. 1188-1197.
Notice of Reasons for Rejection dated Mar. 21, 2017 by the Japanese Patent Office for JP Application No. 2016535474, which was filed on Aug. 20, 2014 and published as 2016527911 on Sep. 15, 2016 (Applicant—Lek Pharmaceuticals) (Original—7 pages // Translated—9 pages).
Singapore Written Opinion dated Feb. 8, 2017 by the Intellectual Property Office of Singapore for SG Application No. 11201601262Q, which was filed on Aug. 20, 2014 and published as 11201601262Q on 3/0/2016 (Applicant—Lek Pharmaceuticals) (10 pages).
Examination Report dated Jan. 18, 2017 by the Australian Patent Office for AU Application No. 2014310555, which was filed on Aug. 20, 2014 and published as AU 2014310555 A1 on Mar. 10, 2016 (Applicant—LEK Pharmaceuticals d.d.) (5 pages).
Decision of Rejection dated Apr. 27, 2018 by the Korean Intellectual Property Office for Patent Application No. 10-2016-7005093, which was filed on Feb. 25, 2016 and published as KR 20160036612 on Apr. 4, 2016 (Inventor—Ficko Trcek et al.; Applicant—LEK Pharmaceuticals D.D.) (Original—5 pages / Translation—7 pages).
Decision of Rejection dated Nov. 7, 2017 by the Japanese Patent Office for Patent Application No. 2016-535474, which was filed on Aug. 20, 2014 and published as JP 2016-527911 on Sep. 15, 2016 (Inventor—Tanja Ficko Trcek; Applicant—LEK Pharmaceuticals D.D.) (Original—5 pages // Translation—7 pages).
Office Action dated Mar. 15, 2018 by the Canadian Intellectual Property Office for Patent Application No. 2915948, which was filed on Aug. 20, 2014 and published as CA 2915948 on Feb. 26, 2015 (Inventor—Tanja Ficko Trcek; Applicant—LEK Pharmaceuticals D.D.) (4 pages).
Communication Pursuant to Article 94(3) EPC dated Mar. 15, 2018 by the European Patent Office for Patent Application No. 14752892.1, which was filed on Aug. 20, 2014 and published as EP 3036254 on Jun. 26, 2016 (Inventor—Tanja Ficko Trcek; Applicant—LEK Pharmaceuticals D.D.) (6 pages).
Written Opinion dated Feb. 5, 2018 by the Intellectual Property Office of Singapore for Patent Application No. 11201601262Q, which was filed on Aug. 20, 2014 (Inventor—Tanja Ficko Trcek; Applicant—LEK Pharmaceuticals D.D.) (7 pages).
Office Action dated Sep. 20, 2017 by the Korean Intellectual Property Office for Patent Application No. 10-2016-7005093, which was filed on Feb. 25, 2016 (Applicant—LEK Pharmaceuticals D.D.) (Original: 8 pages // Translation: 8 pages).

* cited by examiner

Design-Expert® Software
Titer (g/L)

A: Na$_2$SeO$_3$ (μM)

D: ZnCl$_2$ (μM)

CELL CULTURE MEDIUM AND PROCESS FOR CONTROLLING α-AMIDATION AND/OR C-TERMINAL AMINO ACID CLEAVAGE OF POLYPEPTIDES

CROSS-REFERENCE TO RELATED APPLICATIONS

This application is a U.S. National Phase Application of International Application No. PCT/EP2014/067762, filed Aug. 20, 2014, which claims priority to European Patent Application No. 13181027.7, filed Aug. 20, 2013, each of which are hereby incorporated by reference in their entirety.

FIELD OF THE INVENTION

The present invention relates broadly to the technical field of cell culture medium compositions and cell culture processes. In particular, the present invention is directed towards reducing heterogeneity in polypeptides, such as glycoproteins.

BACKGROUND OF THE INVENTION

During the production of recombinant proteins in mammalian cells, several modifications of the proteins take place after their expression (i.e., post-translationally) and, thus, result in a heterogeneity of the recombinant protein product. Since post-translational modifications are not encoded by the nucleotide sequence coding for the protein, but depend mostly on the action of several environmental enzymes, they are difficult to control and keep in tight (desired) specification ranges during the production. The biggest challenge during the manufacturing of especially recombinant therapeutic proteins is therefore to keep the features and quality of the protein product constant.

Within the comprehensive list of all relevant possible quality attributes of polypeptides, the C-terminal α-amidation is ascribed to the group of C-terminal heterogeneity. The processing of C-terminal lysine (Lys) on the heavy chain is one of the most common modifications of recombinant monoclonal antibodies (mAb). The Lys on the C-terminus of the heavy chain can be completely or partially removed by the activity of basic carboxypeptidases (CPs). Removal of one C-terminal Lys residue decreases the molecular weight by 128 Da and increases the positive charge by 1 unit. Partial removal of the C-terminal Lys residues results (due to the quaternary structure of mAbs) in a mixed population of antibodies with zero, one, or two C-terminal Lys residues (Liu et al. 2008). In the absence of Lys, the second amino acid glycine (Gly) can be further removed, and the remaining C-terminal amino acid proline (Pro) is subsequently enzymatically α-amidated.

C-terminal α-amidation is well known and has a major importance in the biologic activity of peptides and proteins. Many neuropeptides need a C-terminal α-amidation step to mature to the active, receptorbinding molecule. The non-amidated analog of leurotoxin for example has a fourfold lower activity in comparison to the leurotoxin comprising C-terminal α-amidated Pro. The stability of the human immunogenic MART-1 peptide in human plasma is markedly increased by C-terminal α-amidation. The C-terminal α-amidation of snake venom increases its lifetime in solution by decreasing its proteolytic degradation and leads to a higher activity in comparison to the unmodified peptide. The tetrapeptide Acetyl-Ser-Asp-Lys-Pro inhibits the proliferation of human and murine primitive hematopoietic cells and is easily degraded by Angiotensin I-Converting Enzyme (ACE). Its C-terminal α-amidated analog cannot be degraded by ACE and its plasma level is 26-fold higher than that of the wild type peptide. C-terminal α-amidation of peptides therefore increases their intrinsic biological and immunological activity, and also their stability.

C-terminal α-amidation is an exclusively enzymatic reaction which is catalyzed by the bifunctional peptidylglycine α-amidating (PAM) enzyme. The first step is the α-hydroxylation of the C-terminal glycine residue by the peptidylglycine α-hydroxylating monooxygenase (PHM, EC 1.14.14.3) domain. The second step is the dealkylation of the α-hydroxyglycine extended peptide to the α-amidated peptide and glyoxylate by the peptidyl α-hydroxyglycine α-amidatinglyase (PAL, EC 4.3.2.5) domain (Metha N M, 2009). For further reading of the enzymatic reaction of the PAM see the international applications PCT/EP2011/069756 or PCT/EP2013/057866, the disclosure content of which is incorporated herein by reference in its entirety.

In this context, several studies on the purified PAM enzyme were performed in order to increase the in vitro and in vivo C-terminal α-amidation. From those studies, a lot of different activators, inhibitors and cofactors were revealed.

EP 0409294A1 describes a substance which acts as a co-factor for the PAM enzyme, has no absorption spectrum above 225 nm, is not a peptide, is not ninhydrin-positive, has a molecular weight less than 1,000 Da, migrates to the positive pole upon electrodialysis and has an amphiphilic structure. The aforementioned inhibitor was used for the preparation of C-terminal α-amidated peptides or proteins (Gunther K, 1990).

Another cofactor for C-terminal α-amidation is described in GB 2233978A. The cofactor for the PAM enzyme is the compound having the formula R—(C=O)$_n$—(CHOR1)$_n$—CH$_2$OR2 wherein R represents a hydrogen atom or an alkyl group, R1 and R2 represents a PO$_3$H$_2$ or SO$_3$H group respectively (Gozzini et al., 1991).

In the paper of Bradbury and coworkers, the in vivo use of the PAM inhibitor 4-phenyl-3-butenoic acid was suggested. The availability of an in vivo inhibitor may allow controlling the degree of C-terminal α-amidation of certain peptide hormones, leading to the reduction in the circulating levels of the active form. In addition, the ability to control the C-terminal α-amidation in vivo may facilitate the studies of intracellular location, transport and storage of the α-amidating enzyme (Bradbury et al., 1989).

The hints that C-terminal heterogeneity can also influence certain properties of recombinant polypeptides are gathered from literature data on C-terminalα-amidated peptides. The process of C-terminal α-amidation elicited scientific and commercial attention by the recognition of the therapeutic potential of α-amidated peptides, such as calcitonin, oxytocine and vasopressin. In recent years, several efficient α-amidating reactions were developed, using preferentially the amidation reaction of pro-hormones catalyzed by an α-amidating enzyme (Kim K H and Seong B L, 2001). In this context, a bifunctional peptidylglycine α-amidating enzyme was successfully used for an in vitro reaction to convert C-terminal extended peptides into peptide hormones displaying a C-terminal α-amidated residue (Merkler D J, 1994). A process for the enzymatic conversion of C-terminal glycine extended peptides into the corresponding des-glycine peptide amide is described in GB 2 220 938 A (Castigliore et al., 1990).

However, little is still known of the effect of C-terminal α-amidation in larger polypeptides like antibodies. Even less or no knowledge is available about the influence of C-terminal heterogeneity of the recombinant polypeptides, such as glycoproteins, in terms of toxicology and immunogenicity, but some extrapolation from the above findings can be performed. Intrinsic antigenicity of the antibody may be altered if the modification changes the surface or the charge of the antibody protein. For antibody target peptides, Maillère and coworkers showed that C-terminal α-amidation of the target peptides provokes a dramatic effect on the corresponding antibody specificity. The antibody response in mice was drastically increased when the peptides showed a C-terminal α-amidation. From those data, the inventor of the present invention assumed that also therapeutic polypeptides, in particular therapeutic antibodies, with C-terminal α-amidation can have altered sensitizing (immunogenic) potential. From the evidence that C-terminal α-amidation increases the lifespan of the peptides and consequently also the T-cell response (Maillère et al., 1995), the extension of the half-life of the antibody may also have a considerable impact on the desired pharmacological efficacy as well as on a potential immunological response to the monoclonal antibody itself.

Thus, as the skilled artisan will appreciate, for the manufacture of recombinantly expressed therapeutic polypeptides such as antibodies, it is particularly important to control post-translational C-terminal modifications of the polypeptides produced, in order to provide i) a constant product quality and a constantly high yield, and/or ii) to increase the efficiency of the production process, and/or iii) to increase and/or fine-tune the physiological activity of the produced polypeptides and the safety of the derived drug, and/or iv) to match the post-translational features of a produced polypeptide to those of a reference polypeptide.

In view to the above, there is a need for a stable and controllable process of controlling or modulating C-terminal heterogeneity during the production of recombinant (glyco-) polypeptides by providing means for the regulation of the PAM and/or CP enzyme activity. Furthermore, there is also a need for high quality non-immunogenic recombinant polypeptides.

Thus, the problem underlying the present invention is the provision of means and methods to control the amount of C-terminal heterogeneity, in particular C-terminal α-amidation in (therapeutic) polypeptides.

The solution to said technical problem is achieved by providing the embodiments characterized in the independent claims of the present invention. The dependent claims are related to preferred embodiments. It is to be understood that value ranges delimited by numerical values are to be understood to include the said delimiting values.

SUMMARY OF THE INVENTION

The present invention provides means and methods for producing non-immunogenic polypeptides, wherein the means and methods are suitable for large scale bioprocesses.

The present invention solves the above mentioned problem by means and methods for modulating (e.g. reducing) C-terminal heterogeneity of a post-translational modification, essentially consisting of α-amidation and/or C-terminal cleavage of amino acid residues of expressed polypeptides by use of a determined concentration of at least one essential trace element or a compound comprising the element as an additive in cell culture medium.

The present invention is based on the surprising finding that essential trace elements are capable of regulating the C-terminal heterogeneity of recombinantly expressed polypeptides.

Put in other words, the present invention relates to a cell culture medium for controlling α-[alpha]-amidation and/or C-terminal cleavage of amino acid residues of at least one expressed polypeptide in a cell culture, wherein the medium comprises at least one essential trace element or a compound comprising the element which acts on/modulates the activity of peptidylglycine [alpha]-amidating monooxygenase (PAM) and/or carboxypeptidase (CP).

In another aspect, the present invention provides a cell culture process for or of controlling α-[alpha]-amidation and/or C-terminal cleavage of amino acid residue of at least one expressed polypeptide, the process comprising as least the steps of: i) adding at least one essential trace element to the cell culture medium comprising a host cell expressing the polypeptide; and ii) fermenting and recovering the polypeptide produced by the host cell. In a preferred embodiment of the present invention, the essential trace element is selected from the group consisting at least of zinc (Cu) selenium (Se) and/or copper (Cu).

In accordance with the present invention, reducing the occurrence of α-amidation at the C-terminal amino acids can either be facilitated by decreasing the formation of C-terminal α-amidated Pro by using a medium with a selenium (Se) concentration from 0.175 μM to about 2.98 μM, or by increasing the proportion of the C-terminal lysine residue on one or preferably all C-termini(us) of the expressed polypeptide(s) by using a medium comprising zinc (Zn) in a concentration ranging from about 0.2 μM to about 20 μM. In a preferred embodiment, a medium comprising 1 μM to 2.4 μM selenium (Se) as well as 3 μM to 15 μM zinc (Zn) is used.

In a preferred embodiment of the present invention, the expression is a heterologous expression and takes place in a eukaryotic cell-based expression system, wherein the eukaryotic cell-based system comprises insect cells, plant cells, mammalian cells, animal cells and lower eukaryotic cells comprising fungi and yeast cells.

In accordance with the present invention, the expression of the polypeptide, i.e., the process of the present invention, takes place in at least one bioreactor (BR) or culture vessel comprising shake flasks (SF), T-flasksrollers, bottles, bags, BRs, and/or spinner flasks.

It is another aspect of the present invention that selenium or a salt thereof is used as an inhibitor for peptidylglycine [alpha]-amidating monooxygenase (PAM) enzyme.

Definitions

Unless otherwise stated, a term as used herein is given the definition as provided in the Oxford dictionary of biochemistry and molecular biology, Oxford University Press, 2006, Print ISBN-13: 9780198529170 Current Online Version: 2008; eISBN: 9780191727641.

For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3$^{rd}$ Ed. (Sambrook et al., Harbor Laboratory Press 2001); Short Protocols in Molecular Biology, 4$^{th}$ Ed. (Ausubel et al. eds., John Wiley & Sons 1999); Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and Clon-Tech. In addition, the disclosure content of the international applications PCT/EP2011/069756 and PCT/EP2013/057866, in particular the methods used in their respective experimental sections, are incorporated herein by reference.

As used herein, "controlling α-amidation" of a biomolecule e.g. an expressed polypeptide in a cell culture means modulating cell culture growth conditions, such as, but not limited to, culture medium, pH, temperature, and growth time until cell harvest, such that the amount of C-terminal non-α-amidated or α-amidated Pro-polypeptide obtained from the cell culture comprises a desired percentage of the entire amount of heterologous polypeptide produced in said cell culture.

As used herein, "controlling C-terminal cleavage of amino acid residue" of a biomolecule, e.g. an expressed polypeptide in a cell culture, means modulating cell culture growth conditions, such as, but not limited to, culture medium, pH, temperature, and growth time until cell harvest, such that the amount of the polypeptide obtained from the cell culture comprises a desired percentage of Lys at their C-terminus (calculated as fraction of the entire amount of heterologous polypeptide produced in said cell culture).

The expressions "acts on" or "modulates the activity of" peptidylglycine [alpha]-amidating monooxygenase (PAM) enzyme and/or carboxypeptidase (CP) means that the essential trace element or a compound comprising the element exhibits an effect on said enzymes which is measurable, such as that the activity or function of the PAM and/or CP enzyme is increased and/or decreased, respectively. The essential trace element or a compound comprising the element can affect the C-terminal α-amidation process by either lowering the rate of catalysis of the PAM enzyme complex. Thereby, the essential trace element either affects or modulates the PAM enzyme complex as such, or affects peptidylglycine alpha-hydroxylating monooxygenase (PHM), which is responsible for cleaving a C-terminal glycine residue, or peptidylamido-glycolatelyase (PAL), which is responsible for the actual α-amidation reaction.

The nucleotide and amino acid sequence of, for example, human PAM are known in the art and can be obtained via public databases, for example, the internet pages hosted by the National Centre for Biotechnology Information (NCBI), including the NIH genetic sequence database Genebank, which also cites the corresponding references available by PubMed Central. For example, as a reference, the human nucleotide and amino acid sequence of PAM are available under accession number Gene ID: 5066 or Accession: AAA36414.1 GI: 189595.

In addition, the essential trace element can affect the rate of carboxypeptidase (CP) (EC 3.4.17.2 and EC 3.4.17.3) by affecting or modulating the activity of the enzyme. CP is an exopeptidase that catalyzes the hydrolytic cleavage of the terminal or penultimate bond at the end of a peptide or polypeptide where the free carboxyl group occurs. The nucleotide and amino acid sequences of human carboxypeptidases are known in the art and can be obtained via public databases, for example, the internet pages hosted by the National Centre for Biotechnology Information (NCBI), including the NIH genetic sequence database Genebank, which also cites the corresponding references available by PubMed Central. For example, as a reference, the human nucleotide and amino acid sequence of carboxypeptidase B (CP) are available under accession number NM004460 and AAB496652.1. Accession: NP001862.2 GI: 4607080.

In an analogous way, the term "decreases the formation" of C-terminal α-amidated Pro means that the α-amidation process or reaction will be reduced, inhibited retarded, controlled, limited or modulated in such a way that less α-amidation compared to a reference sample takes place. α-Pro-amidation effected by the PAM enzyme complex relies basically on the hydrolysis and oxidation of a C-terminal peptide bond between Pro and R of a translated protein, in which R can be one or more than one amino acid residue, for example, Gly, Leu, Ile, Val, or Phe, or Gly-Lys. The reaction is in most cases catalyzed by the PAM enzyme complex (see above). Depending on the expression host and the polypeptide expression conditions, the share of translated proteins carrying at least one post-translational Pro-$NH_2$ can be in the range of $\geq 0$-$\leq 100\%$. Said α-amidation leads to an elevation of protein pH and is thus a basic variant.

In (monoclonal) antibodies or their derivatives, proline (Pro) α-amide (PA) is typically created by post-translational removal of C-terminal lysine and glycine and amidation of the now C-terminal Pro residue, e.g. at the heavy chains of the protein.

The amount of PA can be identified and quantified using various analytical methods by distinguishing the α-amidated variant from the non-α-amidated one by physico-chemical differences such as charge, hydrophobicity or mass. Ion exchange chromatography, as the CEX-CPB method (cation exchange chromatography after digestion by carboxypeptidase B), is an appropriate method for exploiting the charge alteration due to Pro α-amidation. For antibodies, co-elution of Pro-α-amide variants with lysine variants is avoided by removal of lysine residues using carboxypeptidase B digestion prior to chromatographic separation. Additional co-elution with other basic variants, however, can result in a quantification background of several percentages (e.g. 4%). Proline amide variants plus background are termed "Pseudo 1K" for eluting at the chromatographic position of the antibody variant with one C-terminal lysine residue. "Pseudo 2K" encompasses the Proamide variants plus background eluting at the chromatographic position of the antibody variant with two C-terminal lysine residues. The difference to the CEX method (i.e., CEX without lysine removal by CPB digestion) is indicating the amount of antibody variants with lysine residues, termed "Real 1K" and "Real 2K". The quantification by CEX (-CPB) returns the percentage of Proα-amidated antibodies relative to all antibody molecules in a solution. An analytical test method which unambiguously can identify and quantify α-amidated Pro variants is RP-HPLC (reversed-phase high-performance-liquid-chromatography) of endopeptidase (e.g. LysC, trypsin) digested protein, so called peptide mapping, using UV (ultraviolet) or MS (mass-spec) detection. The quantification by RP-HPLC peptide mapping returns for an antibody the percentage of Proα-amidated heavy chains relative to all heavy chains.

"Pseudo 1K" is the variant determined by CEX-CPB where one of the two heavy chains of an antibody (IgG) has a Pro amide at its C-terminus. "Pseudo 2K" is the variant determined by CEX-CPB where both heavy chains of a monoclonal antibody have a Proα-amide at their C-termini. As a skilled person will appreciate, the use of peptide mapping is also preferred for the purpose of the present invention.

As used herein, the term "affects" means to lower, reduce, retard, decrease, inhibit or modulate the activity or function of a protein, enzyme or a chemical or physiological reaction.

"Inhibitor" is any substance which retards or prevents a chemical or physiological reaction or response.

The terms "induce", "inhibit", "increase", "decrease", "lower", "affect", "modulate" "control" or the like, which denote quantitative differences between two states, refer to at least statistically significant differences between the two states and do not necessarily indicate a total elimination of the expression or activity such as α-amidation of a cell or a polypeptide.

Such terms are applied herein to, for example, levels of expression, amounts, and levels of activity.

As used herein, the term "heterologous(ly)" means (a) obtained from a cell or an organism through isolation and introduced into another cell or organism, as, for example, via genetic manipulation or polynucleotide transfer, and/or (b) obtained from a cell or an organism through means other than those that exist in nature, and introduced into another cell or organism, as, for example, through cell fusion, induced mating, or transgenic manipulation. A heterologous material may, for example, be obtained from the same species or type, or a different species or type than that of the organism or cell into which it is introduced.

"Cell-based expression system" refers to expression systems or portions thereof or polynucleotides introduced in accordance with of the invention (e.g., transfected, infected, or transformed) into a host cell or host cell lysate for the production of a polynucleotide and/or polypeptide of the invention.

"Host cell" is a cell, including but not limited to a eukaryotic or prokaryotic cell, such as mammalian cell, animal cell, insect cell, plant cell, algae cell, fungus cell, bacterial cell or cell of a microorganism into which an isolated and/or heterologous polynucleotide sequence has been introduced (e.g., transformed, infected or transfected) or is capable of taking up exogenous nucleic acid (e.g., by transformation, infection or transfection). Any cell which is capable of expressing an integrated (in the genome) or a free replicating (e.g. plasmid) transgene or comprises endogenously or heterologously a PAM and/or CP enzyme or a homolog and/or ortholog thereof, having substantially the same function, is suitable in accordance with the meaning of the present invention; see e.g., US patent application 2008/0305523 for suitable fungus cells; U.S. Ser. No. 08/477,559 for suitable plant cells; EP2560479 for suitable algae cells; US 2011/0117643 for suitable animal cells; US patent 20130034897 for suitable bacterial cells as well as EP1050582 for suitable microorganism cells.

The term "eukaryotic" cell shall refer to a nucleated cell or organism, encompassing but not limited to insect, plant, algae, fungus, mammalian and animal.

"Cell culture" or "culture" means the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture", "organ culture", "organ system culture" or "organotypic culture" may occasionally be used interchangeably with the term "cell culture". The media of the present invention can be used to culture any adherent cell (i.e., a cell which adheres to the culture vessel) and any cell which grows in suspension culture.

As used herein, the expressions "cell culture medium" or "culture medium" or "fermentation medium" or "cell culturing" refer to a nutrient solution used for growing and shall refer to all kinds of media which are used in the context of culturing cells. Typically, a cell culture medium comprises amino acids, at least one carbohydrate as an energy source, trace elements, vitamins, salts and possibly additional components (e.g. in order to influence cell growth and/or productivity and/or product quality). It is known that improved levels of recombinant polypeptide expression can be obtained from cells grown in serum-free medium, relative to the level of expression seen in cells grown in medium supplemented with serum. Thus, the medium of the present invention can either be serum-free or supplemented with 0.5, 1, 2, 3, 4, 5, 10, 15 or 20% of serum.

As used herein, the terms "feed", "feed medium" or "feed solution" refer to a kind of cell culture medium or to a solution of specific components, which is added as supplement to a cell culture during the process usually in order to influence cell growth and/or productivity and/or product quality.

As used herein, the term "cell culture fluid" shall refer to the actual liquid in which the cells are being cultured. This means that said fluid can contain, in contrast to a cell culture medium or feed according to the above definition, metabolites produced by the cells, cell debris, cellular proteins (e.g., enzymes or recombinant protein).

As used herein, the expression "amount of α-amidated amino acid residues" relates to α-amidated amino acid residues formed during or after protein expression at the C-terminus of the protein. This relates, specifically, to the amount of α-amidated Pro. Under certain circumstances, Pro residues in a polypeptide can be α-amidated post-translationally, leading to the formation of, e.g., Pro-α-amide (Pro-$NH_2$). This is unwanted in some cases, e.g. when the amount of Pro-α-amide in the polypeptide to be produced is higher, or lower, than in a reference polypeptide.

As used herein, the term "a compound comprising" the essential trace element, or the ion, or a salt thereof, of the essential trace element relates to any organic or inorganic compound, which has, in a physiological setting (e.g., a cell culture fluid), the same potential effect as the essential trace element defined below.

A (trace) element is considered "essential" if a dietary deficiency of the element consistently results in a suboptimal biologic function in a host, comprising plant, animal and/or human that is preventable or reversible by intake of physiologic amounts of that element. Phosphorus (P), potassium (K) and sulphur (S) are regarded as macronutrients in all living systems. Calcium (Ca) and magnesium (Mg) are required in relatively large quantities. The following elements are needed by a living organism only in trace or ultra-trace amounts and are also termed "essential trace elements" in accordance with the present invention: arsenic (As), boron (B), chromium (Cr), cobalt (Co), copper (Cu), iron (Fe), fluorine (F), lithium (Li), iodine (I), manganese (Mn), molybdenum (Mo), nickel (Ni), selenium (Se), strontium (Sr), silicon (Si), sulphur (S), tin (Sn), vanadium (V), zinc (Zn), and optionally the rare earth elements. In accordance with the present invention, the use a certain amount of selenium (Se), zinc (Zn) and/or copper (Cu) is preferred. In addition, every possible oxidation state of an essential trace element as well as an isotope or radical or a mimic, exhibiting the same function on C-terminal heterogeneity as Se, Zn or Cu or any combination thereof, can be used in accordance with the present invention.

The "oxidation state" of an atom in a molecule gives the number of valence electrons it has gained or lost. Essential trace elements can be added alone or in any kind of combination, at any time either during the production of the medium or added prior to the use of the medium, simultaneously in rotifers in both short term enrichments (3 h) or during batch cultures using either organically bound (for example, to an amino acid, a protein or other biomolecule) or complex or inorganic mineral sources. In addition, the essential trace elements can be present in culture as free ions, either intracellular or extracellular, or may be complexed.

In this context, "trace" means that an element as defined above, is present in only a trace concentration. A trace concentration or level may be a $<10^{-5}$, $<10^{-6}$, $<10^{-7}$ or $<10^{-8}$ or $<10^{-9}$ M. A trace element or any other ingredient or compound is intentionally present in a medium, composition, or fluid, either by known addition or by intentional use of a non-pure material for adding the trace "impurity". Thus, the medium, composition, or fluid will have a known or defined amount of the trace element.

An "effective amount" refers to an amount (dose or concentration or number of molecules used of a respective compound, enzyme or ion) effective in mediating an effect, particular a desired effect, either taken in one dose or in any dosage or route, taken alone or in combination with other agents.

The term "pharmaceutical preparation and/or composition", as used herein, indicates a composition suitable for or adapted to administration to a mammal, especially a human.

The terms "(glyco-) polypeptide", "peptide", and "(glyco-) protein" are used interchangeably herein to refer to a polymer of amino acid residues, optionally having oligosaccharide chains (glycans) covalently attached. The terms apply to amino acid polymers in which one or more amino acid residue(s) is/are (an) analogue(s) of a corresponding naturally occurring amino acid, as well as to naturally occurring amino acid polymers. The terms also include variants of the traditional peptide linkage joining the amino acids and thereby making up the polypeptide.

As used herein, the term "antibody" refers to monoclonal antibodies (mAbs), multispecific antibodies, human antibodies, humanized antibodies, synthetic antibodies, chimeric antibodies, polyclonal antibodies, camelized antibodies, single-chain Fvs (scFv), single chain antibodies, immunologically active antibody fragments (e.g., antibody fragments capable of binding to an epitope, e.g., Fab fragments, Fab' fragments, F(ab')$_2$ fragments, Fv fragments, fragments containing either a VL or VH domain or a complementary determining region (CDR) that immune specifically binds an antigen, etc.), bi-functional or multi-functional antibodies, disulfide-linked bispecific Fvs (sdFv), intrabodies, and diabodies, and epitope-binding fragments of any of the above. In particular, the term "antibody" is intended to encompass immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG$_b$ IgG$_2$, IgG$_3$, IgG$_4$, IgAi and IgA$_2$) or subclass.

The term "antibody derivative or fragment" refers to a portion of a full-length antibody, generally the target binding or variable region. Examples of antibody fragments include Fab, Fab', F(ab')2 and Fv fragments. An "Fv" fragment is the minimum antibody fragment which contains a complete target recognition and binding site. This region consists of a dimer of one heavy and one light chain variable domain in a tight, non-covalent association (VH—VL dimer). It is in this configuration that the three CDRs of each variable domain interact to define a target binding site on the surface of the VH—VL dimer. Collectively, the six CDRs confer target binding specificity to the antibody. However, even a single variable domain (or half of an Fv comprising only three CDRs specific for a target) has the ability to recognize and bind a target, although at a lower affinity than the entire binding site. "Single-chain Fv" or "scFv" antibody fragments comprise the VH and VL domains of an antibody, wherein these domains are present in a single polypeptide chain. Generally, the Fv polypeptide further comprises a polypeptide linker between the VH and VL domains which enables the scFv to form the desired structure for target binding.

With the term "fusion protein", peptides, polypeptides as well as proteins are meant which are created through the joining of two or more genes which originally coded for separate proteins. Translation of this fusion gene results in a single polypeptide with functional properties derived from each of the original proteins. The meaning of this term encompasses chimeric and humanized antibodies, as well as constructs consisting, e.g., of a receptor domain and an IgG Fc segment.

As used herein, the expression "non-antibody proteins" relates to physiologically active proteins which are not antibodies. Such definition encompasses, among others, insulin, somatropin, erythropoietin, interferon alpha or G-CSF, tissue plasminogen activator (tPA), factor VIII, and/or interleukin 2, or fragments or derivatives thereof.

The terms "variant", "derivative" and "analog", when referring to antibodies or antibody polypeptides of the present invention, include any polypeptides which retain at least some of the antigen-binding properties of the corresponding native binding molecule, antibody, or polypeptide, still having some structural relationship to, and retaining some functional property of, the common antibody concept, e.g. scFv, as well as bi-, tri- or higher specific antibody constructs, pegylated antibody constructs and the like.

Similar concepts apply to "fragments or derivatives of a protein" in the meaning of the present invention.

The term "kit" refers to a collection of materials, preferably a packaged collection of materials (preferably related materials) to perform a particular function (e.g. to run an assay, to express a protein, to culture a cell, to purify a polypeptide, etc.). A kit may optionally comprise instructional materials describing the use of the materials present in the kit.

As used herein, the term "concentration" of a given ion or a salt thereof, such as "selenium or a salt thereof", "zinc or a salt thereof" and/or "copper or a salt thereof" denotes the final concentration of the selenium and/or zinc and/or copper ion in a cell culture medium (e.g. cell culture medium, or feed medium, or feed solution), or in a cell culture fluid.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

The invention provides a cultivation medium as well as a method of producing polypeptides, wherein said polypeptides exhibit a reduced amount of C-terminal α-amidated Pro and/or an increased amount of C-terminal Lys. By not inhibiting growth and productivity, selenium (Se) and zinc (Zn) addition in specified concentrations can be used for the production of high quality, non-immunogenic therapeutically useful (glyco-)polypeptides using, e.g., large scale bioprocesses.

Thus, the present invention concerns a cell culture medium for or of controlling α-amidation or C-terminal cleavage of amino acid residues of at least one expressed polypeptide in a cell culture, wherein the medium comprises, essentially consists of, or consist of at least one essential trace element or a compound comprising the element which acts on peptidylglycine [alpha] α-amidating monooxygenase (PAM) or carboxypeptidase (CP) enzyme.

Despite of all the available data about many activators and inhibitors of the PAM enzyme, the inventor of the present invention surprisingly discovered that selenium has a major influence on PAM activity. By increasing the concentration of selenium in the production (fermentation) media above the so far known maximum concentration of selenium of about 0.1 µM comprised in a very few commercially available media (IMDM 0.067 µM, advanced DMEM 0.03 µM, advanced RPMI 0.03 µM, advanced MEM 0.03 µM), the inventor was able, as shown in the Examples of the present invention, to inhibit the activity of the PAM enzyme, and the resulting recombinant polypeptide product had a significantly reduced amount of C-terminal α-amidation.

In addition, by decreasing the zinc ion concentration in the production (fermentation) media the activity of CP was inhibited, leading to an increased amount of C-terminal Lys and—consequently—to an even lower amount of C-terminal α-amidation. Thus, the present invention provides the surprising finding that by modifying the concentration of two essential trace elements (additives) in the production media, a product with reliable C-terminal heterogeneity can be produced.

Figure 11:
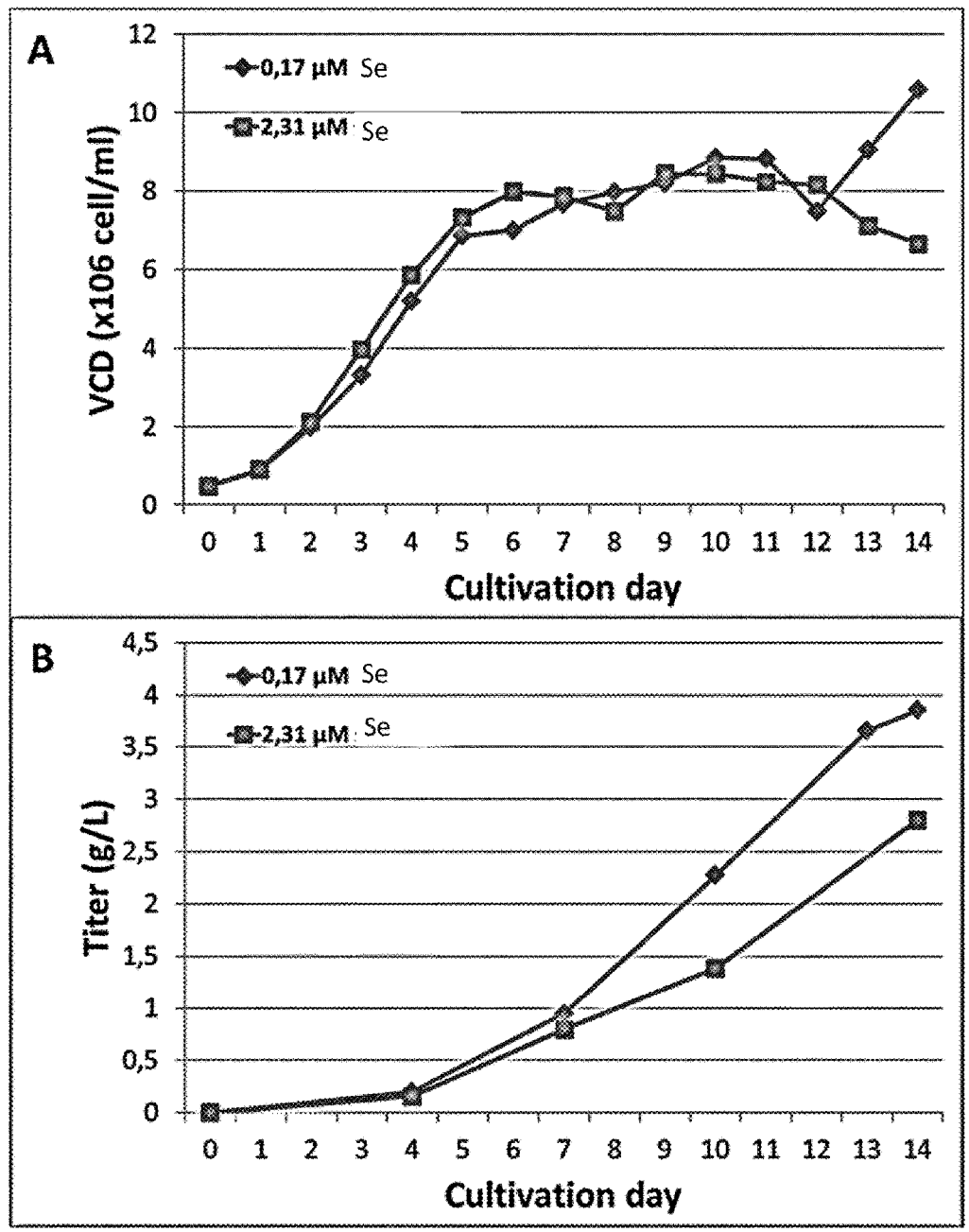
FIG. 11: Confirmation experiment performed in a BR system. The effect of increased selenium concentration on the cell growth (A) and productivity (B) is depicted.

In the first "univariate" approach in accordance with the present invention, several well-known inhibitors of the PAM enzyme were tested, but the majority of them led to the drop of productivity or poor cell culture performance. In the second "multivariate" approach the production media were split into several building blocks and tested in the design of experiment (DOE) manner. The inventor surprisingly found that selenium has a major negative influence on the in vivo formation of C-terminal α-amidated Pro. By increasing the selenium concentration in the production media to the sub-toxic level, the cell culture performance and productivity remain acceptable and—most importantly—the activity of the PAM enzyme can be inhibited. Consequently, the resulting polypeptide product showed a significantly decreased amount of C-terminal α-amidated Pro (see Example 11 as well as FIGS. 11 and 12).

In view of these findings, the present invention naturally extends to a cell culture process for or of controlling α-amidation and/or C-terminal cleavage of amino acid residue of at least one expressed polypeptide, the process comprising or essentially consisting of as least the steps of: adding at least one essential trace element to the culture medium comprising or essentially consisting of a host cell producing a polypeptide; and fermenting and recovering the polypeptide.

Put in other words, the present invention relates to a method of reducing heterogeneity of recombinantly expressed polypeptides, comprising antibodies obtained by said cell culturing, said method comprising the steps of adding at least one essential trace element capable of reducing and/or inhibiting the activity of peptidylglycine [alpha]-amidating monooxygenase (PAM) or carboxypeptidase (CP) enzyme into the cell culture medium to obtain said polypeptide with reduced heterogeneity. In addition, another essential trace element which is capable of reducing and/or inhibiting the activity of CP enzyme is added.

In a preferred embodiment, the essential trace element, or the addition thereof, decreases the amount of C-terminal [alpha]-amidated proline or increases the amount of C-terminal lysine.

In accordance with the present invention, the person skilled in the art will understand that the medium can be supplemented with the essential trace element(s) or with a mimic of the essential trace element(s) which exhibit(s) the same effect as the essential trace element(s). In accordance with the present invention, the essential trace element is an ion or a salt thereof or a compound comprising the ion or a salt thereof. In a preferred embodiment, the essential trace element is selected from the group consisting of (Se), zinc (Zn) and/or copper (Cu). As defined above, any suitable salt of Se, Zn and/or Cu can be used or any inorganic or organic compound containing, comprising or essentially consisting of a selenium (Se), zinc (Zn) and/or copper (Cu) ion, as long as the respective compound exhibits an effect on C-terminal Pro α-amidation or C-terminal lysine cleavage within the meaning of the present invention.

Figure 9:
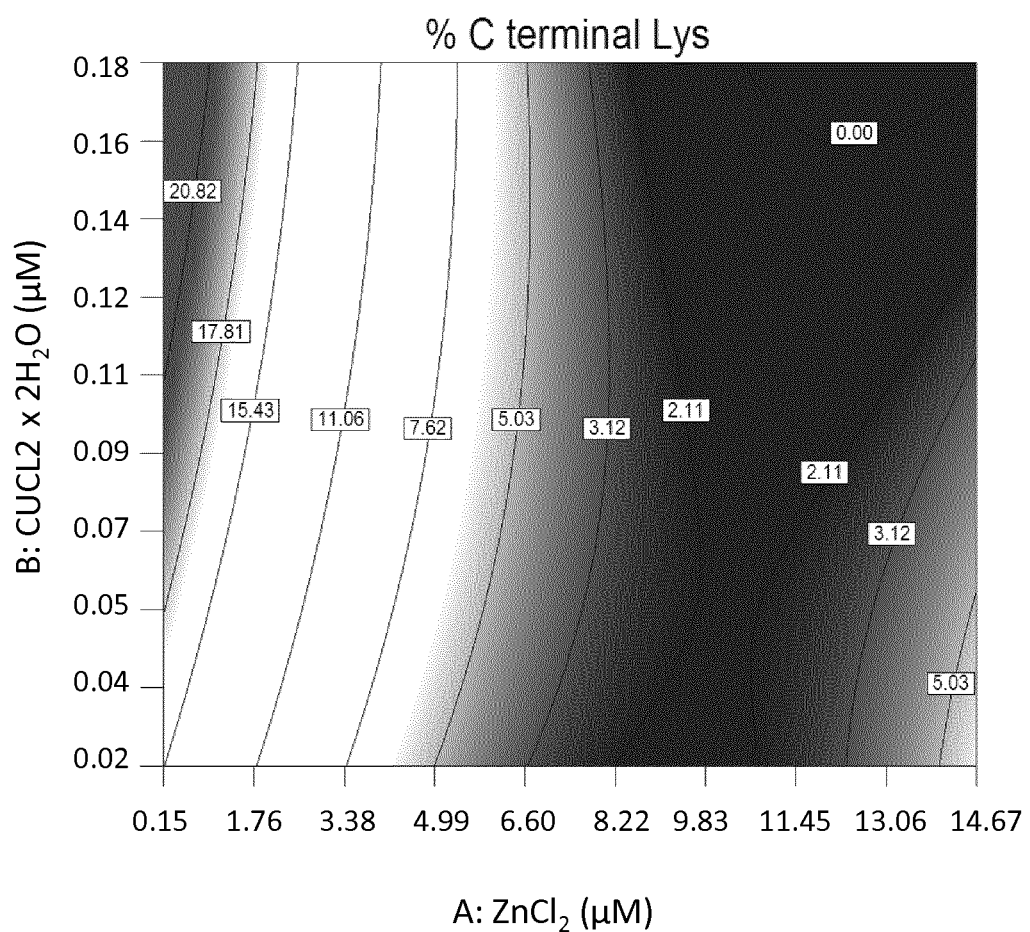
FIG. 9: Contour diagram created by DOE software where the effects of zinc on the amount of C-terminal Lys is presented. Increased zinc concentrations in the fermentation media resulted in decreased amount of C-terminal Lys indicating an increased activity of the CP enzyme.

During the DOE experiments, a second surprising observation was made. Zinc was found to be a major in vivo activator of the CP enzyme as shown in Examples 5 and 9 and FIGS. 5, 6 and 9. By decreasing the zinc concentration in the production media, the activity of the CP enzyme can be reduced and the corresponding recombinant product showed an increased amount of C-terminal Lys (see Example 11 as well as FIG. 14). The increase of the concentration of selenium and the reduction of the concentration of zinc result in a recombinant polypeptide product having C-terminal heterogeneity comparable to a reference product with predetermined C-terminal heterogeneity in terms of α-amidated Pro and/or Lys. By modulating the Se and Zn concentration in the production medium, the C-terminal heterogeneity in terms of α-amidated Pro and/or Lys of the produced protein can be adjusted to the respective C-terminal heterogeneity of a reference protein. The amount of C-terminal α-amidated Pro can be decreased and the amount of C-terminal Lys can be increased.

In addition, the inventor of the present invention surprisingly found out that even at low zinc concentrations in a cell culture medium, the growth of the host cells as well as the respective polypeptide expression is not impaired.

Hence, the present invention relates to a medium or a process, wherein the essential trace element or the addition thereof, decreases the formation of C-terminal α-amidated Pro or increases the amount of C-terminal Lys. In a preferred embodiment, selenium is added in an effective amount to the cell culture medium or the medium used in the process of the present invention, for controlling α-amidation. In a further preferred embodiment of the present invention, zinc is added in an effective amount to the cell culture medium or the medium used in the process for controlling C-terminal cleavage of amino acid residues and/orfor controlling α-amidation.

It will be apparent to one of skill in the art that the at least one essential trace element as defined above, preferably selenium, can be added to the medium at the beginning of the culturing process or a certain concentration of selenium is already contained in the medium, in order to keep the α-amidation of the expressed polypeptides at a low level, i.e. reduce or inhibit the C-terminal α-amidation process. Thereby, the process of the present invention can be used to modulate, control, reduce or lower the heterogeneity of recombinantly expressed polypeptides such as proteins or peptides which exhibit on their C-terminal end an alpha Pro amino residue. Reducing the zinc concentration in the medium compared to a very few commercially available media which exhibit 0.173 μM selenium, and/or 2.04 μM copper and/or 22 μM zinc ions, will additionally improve the reduction of C-terminal α-amidation as outlined above. Further improvement can be achieved when the cells expressing the desired polypeptide are additionally cultivated in the presence of a low copper ion concentration, e.g. below 2.04 μM. In case it is desired to have a heterogeneous population of α-amidated and non-α-amidated/deamidated polypeptides, the selenium additive can be added to the cell culture medium at a later time point during cultivation.

Thus, the present invention provides, in some embodiments, a cell culture medium or processes of producing a glycoprotein in cell culture by adding an effective amount of selenium, and/or zinc and/or copper to a culture medium to modulate C-terminal α-amidation and/or C-terminal cleavage of amino acid residue of the glycoproteins. In some embodiments, the effective amount is enough to inhibit or decrease PAM activity. In some embodiments, the effective amount is sufficient to inhibit, affect, reduce or lower the CP activity.

In a preferred embodiment of the present invention, selenium is used for controlling α-amidation.

The selenium compound that provides selenium ions for use in the present invention may be any physiologically acceptable selenium salt including the water soluble (including sparingly water soluble) organic and inorganic selenium salts or esters. Other preferred compounds are selenite, selenate, selenic, selenous or selenious acid. Other selenium compounds such as selenium methionine, selenium cysteine, selenite fumarate, 2-seleno-5-methylaminomethyl-uridine and seleno-proteins can be used. In accordance with the present invention, the selenium ions are used preferably in the form of sodium selenite. Since sodium selenite is a selenium compound with strong toxicity, sodium selenite can be replaced with a different selenium form, which has the same bioactivity as high doses of sodium selenite but with lower toxicity. Further suitable compounds either containing selenium or compounds mimicking the function of selenium in terms of its ability to control α-amidation, e.g. an isotope or radical of selenium, or an isotope or radical of elements belonging to the same chemical group in the periodic system, are defined above or well known to the skilled person.

In a further preferred embodiment of the present invention, zinc is used for controlling C-terminal cleavage of amino acid residue and/or for controlling α-amidation.

The zinc compound that provides zinc ions for use in the present invention may be any physiologically acceptable zinc salt including the water soluble (including sparingly water soluble) organic and inorganic zinc salts or esters. Other preferred compounds are sparingly soluble zinc salts, of which zinc citrate, zinc chloride, or zinc nitrate are most preferred. Examples of suitable zinc salts that may be employed include: zinc acetate, zinc fluoride, zinc ammonium sulfate, zinc formate, zinc bromide, zinc iodide, zinc chloride, zinc nitrate, zinc chromate, zinc phenol sulfonate, zinc citrate, zinc salicylate, zinc dithionate, zinc sulfate, zinc fluosilicate, zinc gluconate, zinc tartarate, zinc succinate, zinc glycerophosphate, and mixtures thereof. Zn-containing compounds which may be used include but are not limited to $ZnCl$, $Zn(NO_3)_2$, $ZnBr$, and $ZnSO_4.7H_2O$. Preferably, the Zn compound used is zinc chloride ($ZnCl_2$ with or without× $2H_2O$) or zincsulfate.$7H_2O$ ($ZnSO_4.7H_2O$). Typically, the concentration of Zn is given for the 1× medium of the present invention. In accordance with the present invention, the zinc ions are used preferably in the form of zinc chloride ($ZnCl_2$). Also preferred in accordance with the present invention is any organic or inorganic compound which is suitable of reducing the zinc concentration in a medium to a concentration wherein the CP activity is reduced or lowered as defined above.

As shown in the Examples, the addition of very low amounts of copper ions to the medium of the present invention or the addition or use thereof in the process of the invention results in a combinatory or synergistic effect, wherein the amount of non-α-amidated Pro residues of the produced polypeptides could be even further increased. Thus, it is preferred in accordance with the present invention that the cell culture medium or the medium used in the process of the present invention comprises copper in an effective amount or the addition thereof.

The copper compound that provides copper ions for use in the present invention may be any physiologically acceptable copper salt including the water soluble (including sparingly water soluble) organic and inorganic copper salts or esters. Other preferred copper salts or esters are well known such as copper sulphate, copper salicylate $C_7H_4O_3Cu—H_2O$, copper hydroxide or copper oxychloride. In accordance with the present disclosure, the copper ions are used preferably in the form of copper chloride.

Polymeric selenium, zinc or copper containing main chain block copolymers, organic compounds which release the bound selenium, zinc or copper ions into the media are well known in the art.

Hence, in view of the experiments performed in accordance with the present invention and illustrated in the Examples, it is an object of the present invention to provide a process or medium, wherein the medium comprises at least one of the following essential trace elements or a combination thereof: selenium (Se) in a concentration ranging from above 0.175 µM to about 2.98 µM, preferably 1 µM to 2.4 µM, and/or zinc (Zn) in a concentration ranging from about 0.2 µM to about 20 µM, preferably above 3 µM to 15 µM, and/or copper (Cu) in a concentration ranging from about 0.18 µM to about 0.8 µM.

In some embodiments, the concentration of zinc (Zn), selenium (Se) and/or copper (Cu) may be, for example, greater than one or more of the following values: 0.005 µM 0.006 µM, 0.007 µM, 0.008 µM, 0.009 µM, 0.01 µM, 0.02 µM, 0.03 µM, 0.04 µM, 0.05 µM, 0.06 µM, 0.07 µM, 0.08 µM, 0.09 µM, 0.10 µM, 0.11 µM 0.12 µM, 0.13 µM 0.14 µM, 0.15 µM, 0.16 µM, 0.17 µM, 0.18 µM, 0.19 µM, 0.20 µM, 0.21 µM, 0.22 µM, 0.23 µM, 0.24 µM, 0.25 µM, 0.30 µM, 0.35 µM, 0.40 µM, 0.5 µM, 1.0 µM, 1.1 µM, 1.2 µM, 1.3 µM, 1.4 µM, 1.5 µM, 1.6 µM, 1.7 µM, 1.8 µM, 1.9 µM, 2.0 µM, 2.1 µM, 2.2 µM, 2.3 µM, 2.4 µM, 2.5 µM, 2.6 µM, 2.7 µM, 2.8 µM, 2.9 µM, 3.0 µM, 5.0 µM, 10.0 µM, 11.0 µM, 12.0 µM, 13.0 µM, 14.0 µM, 15.0 µM, 16.0 µM, 17.0 µM, 18.0 µM, 19.0 µM, 20.0 µM, 21.0 µM, 22.0 µM, 23.0 µM, 24.0 µM, 25.0 µM, 26.0 µM, 27.0 µM, 28.0 µM, 29.0 µM or 30.0 µM.

It should be noted that in feed solution, the concentration of selenium, zinc and/or copper can be significantly higher than in a cell culture medium, or in a cell culture fluid, e.g. up to 3 µM.

The essential trace elements as defined above can be added to the medium at the beginning of the cell culture process. Alternatively, the essential trace elements can be supplemented during the cell culture process, e.g., as ingredient(s) of a feed medium. In a preferred embodiment, the ions are added separately or in a combination in batch to the fed batch culture system with or without other appropriate nutrients as described herein or known to those skilled in the art of mammalian cell culture.

Hence, in one embodiment, the medium or process of the present invention, the amount of C-terminal α-amidated Pro of the expressed polypeptide is decreased compared to the use of standard media comprising 2.04 µM copper and 0.173 µM selenium. In a preferred embodiment of the present invention, 2.3 µM±0.6 µM selenium is present in the medium, preferably wherein the medium also comprises 0.4 µM±0.5 µM copper.

In line with the above, the skilled person will appreciate that the medium further comprising zinc and/or copper in an effective amount will be capable of further reducing, inhibiting or lowering the rate, amount or proportion of α-amidation of C-terminal amino acids.

In the context of the present invention, the term reducing the zinc concentration to "minimum level" is to be understood as a level, wherein the cells can still grow and are capable of producing polypeptides, such as glycoproteins, in a sufficient amount. Sufficient amount in terms of cell growth and productivity is herein to be understood as at least 1 g/L are produced after 14 days of cultivation, and at least $2\times10^6$ cell/ml of cells are grown after 14 days of cultivation, respectively.

As a result, glycoproteins can be produced which exhibit an increased, i.e. higher, amount of C-terminal Lys compared to the use of some standard media exhibiting 22 µM zinc ions. Therefore, the PAM enzyme cannot α-amidate the C-terminal Pro residue, due to the presence of the Lys amino acid, thus leading to an increased production/amount of non-α-amidated glycoproteins.

Accordingly, the medium or process of the present invention relates to the use of zinc for or of controlling C-terminal cleavage of amino acid residue and/or for or of controlling α-amidation. In addition, in one embodiment in accordance with the present invention, the amount of C-terminal Lys of the expressed polypeptide is increased compared to the use of standard media having 22 µM zinc ions, preferably wherein 2.3 µM to 11 µM±0.5 µM is present in the medium. In a preferred embodiment, zinc is present in a concentration of above 3 µM, wherein "above" indicates that zinc ion concentration is above 3.00 µM, for example 3.05 µM, 3.1 µM, 3.2 µM, 3.3 µM, 3.4 µM, 3.5 µM. The term "above" is equivalently defined for the concentration of selenium as well as copper. In a further embodiment of the present invention, the amount of C-terminal Lys is increased to 10%, 15%, preferably to 16%±0.79% compared to the use of a standard media having 22 µM zinc.

The polypeptide obtained from the process of the present invention can be used for the preparation of a pharmaceutical preparation and/or composition, either as a diagnostic or a therapeutic composition. Thus, the obtained polypeptides can be administered together with other components of biologically active agents such as pharmaceutically acceptable surfactants, recipients, carriers, diluents and vehicles and/or a further diagnostic or therapeutic compound such as a marker or a drug attached or linked to the polypeptide. Optionally in any combination with an amount of Se, Zn and/or Cu or compounds of the composition as outlined below.

The medium or process of the present invention may be used in any culture process, but is especially preferred for eukaryotic cells, especially biomolecule producing cells. Bioproduction may include vaccine production, protein production, glycoprotein production, antibody or antigen production, nucleic acid production, organelle production, lipid production, carbohydrate production, etc. Preferred in accordance with the present invention is the polypeptide production.

The polypeptide is produced by an expression system also termed cell-based expression system, wherein a host cell cultivated in the medium of the present invention expresses the polypeptide. In a preferred embodiment, the polypeptide is provided by inducing heterologous expression of a gene coding for the respective polypeptide in a host cell. In another preferred embodiment of the present invention, said heterologous expression takes place in a cell based expression system. Such a cell-based expression system denotes a host cell used in the process according to the present invention in order to allow the expression of the polypeptide in the presence of the medium of the present invention.

A host cell as defined above contains a nucleic acid such as an active gene coding for the respective polypeptide and this nucleic acid is transcribed and translated during culture of the cell in the medium. The gene can be introduced into this host cell as an exogenous gene, preferably with regulation (regulatory) elements (see, e.g., EP-B 0 148 605) or can already be present in the host cell as an active endogenous gene or can become activated as an endogenous non-active gene. Such an activation of endogenous genes can be achieved by the specific introduction of regulation (regulatory) elements into the genome by homologous recombination, see for further reading international applications WO 91/09955 and WO 93/09222. In a preferred embodiment of the present invention, said expression is a heterologous protein expression.

Without intending to be bound by theory, the medium or process using the medium of the present invention is suitable for cultivating any of the above defined host cells capable of expressing a polypeptide carrying at least one post-translational Pro-NH$_2$. The skilled person is well aware of suitable host cell-specific medium compositions and cultivation methods.

In a further preferred embodiment, said eukaryotic cell-based expression system of the present invention comprises a eukaryotic host cell, wherein the eukaryotic cell is selected from the group consisting of or essentially consisting of insect cells, plant cells, algae cells, fungus cells, mammalian cells, animal cells and/or lower eukaryotic such as filamentous fungus or yeast cells. In a preferred embodiment, said eukaryotic cell-based expression system is a mammalian system.

The insect, plant, algae, fungus, mammalian, animal and/or lower eukaryote species which can be used as a cell-based expression system in accordance with the present invention may be any of said species which can be genetically manipulated to carry a transgene of interest and are well known in the art.

In another preferred embodiment, said eukaryotic cell-based expression system essentially consists of or comprises or is selected from the group consisting of:
Baby hamster Kidney cell lines (e.g., BHK21)
Chinese hamster ovary cell lines (e.g., CHO-K1, CHO-DG44, CHO-DXB, or CHO-dhfr$^-$)
Murine myeloma cell lines (e.g., SP2/0)
Mouse myeloma cell lines (e.g., NS0)
Human embryonic kidney cell lines (e.g., HEK-293)
Human-retina-derived cell lines (e.g., PER-C6), and/or
Amniocyte cell lines (e.g., CAP).

Preferably, hamster cell-based expression systems are being used. BHK21 ("Baby Hamster Kidney") cells belong to a quasi-diploid established line of Syrian hamster cells, descended from a clone from an unusually rapidly growing primary culture of newborn hamster kidney tissue. Non limiting examples for BHK-21 cell lines which are commercially available and can be used in the context of the present invention are BHK-21 (C-13); BHK21-pcDNA3.1-HC; BHK570; Flp-In-BHK Cell Line; and/or BHK 21 (Clone 13) hamster cell line.

Chinese hamster ovary (CHO) cells are a cell line derived from the ovary of the Chinese hamster. They are often used in biological and medical research and commercially in the production of therapeutic proteins. They were introduced in the 1960s and were originally grown as a monolayer culture. Today, CHO cells are the most commonly used mammalian hosts for industrial production of recombinant protein therapeutics and are usually grown in suspension culture.

Non limiting examples for CHO cell lines which are commercially available and can be used in the context of the present invention are FreeStyle CHO-S cells; ER-CHO Cell Line; CHO 1-15 500 CHINESE HAM; CHO-DXB, CHO-dhfr-, CHO DP-12 clone#1934; CHO-CD36; CHO-ICAM-1; CHO-K1; Ovary; HuZP3-CHOLec3.2.8.1; xrs5; CHO-K1/BB2 Cells; CHO-K1/BB3 Cells; CHO-K1/EDG8/Galpha15 Cells; CHO-K1/M5 Cells; CHO-K1/NK1 Cells; CHO-K1/NK3 Cells; CHO-K1/NMUR1 Cells; CHO-K1/NTSR1 Cells; CHO-K1/OX1 Cells; CHO-K1/PAC1/Gal5 Cells; CHO-K1/PTAFR Cells; CHO-K1/TRH1 Cells; CHO-K1/V1B Cells; 5HT1A Galpha-15-NFAT-BLA CHO-K1 Cell Line; AVPR2 CRE-BLA CHO-K1 Cell Line; CHO-S Cells SFM Adapted; DG44 Cells; Flp-In-CHO Cell Line; GeneSwitch-CHO Cell Line; NFAT-bla CHO-K1 Cell Line; T-REx-CHO Cell Line; GenoStat CHO K-1 Stable Cell Line; GenoStat CHO K-1 Stable Cell Line Kit; CHO-K1 Cell Line hamster, CHO-PEPT1 Cell line. In a particularly preferred embodiment, the hamster cell-based expression system is a CHO-dhfr$^-$-cell line.

In another preferred embodiment of the present invention, said heterologous expression takes place in a eukaryotic cell-based expression system. Preferably, the expressed protein is at least one protein selected from the group consisting of:

an antibody, or a fragment or derivative thereof,
a fusion protein, and/or
non-antibody proteins.

Preferably, the processes and media according to the present invention are suitable for the (recombinant) production of proteins comprising amino acid sequences identical to or substantially similar to all or part of one of the following proteins: an Flt3 ligand, a CD40 ligand, erythropoies is stimulating proteins like erythropoietin (EPO), darbepoetin including darbepoetin alfa, and thrombopoietin, calcitonin, leptin, a Fas ligand, a ligand for receptor activator of NF-kappa B (RANKL), a tumour necrosis factor (TNF)-related apoptosis-inducing ligand (TRAIL), thymicstroma-derived lymphopoietin, granulocyte colony stimulating factor, granulocyte-macrophage colony stimulating factor (GM-CSF), growth factors including mast cell growth factor, stem cell growth factor, epidermal growth factor, keratinocyte growth factor, megakaryote growth and development factor, RANTES, growth hormone, insulin, insulinotropin, insulin-like growth factors, parathyroid hormone, interferons including α-interferon, β-interferon, and γ-interferon, nerve growth factor, brain-derived neurotrophic factor, synaptotagmin-like proteins (SLP1-5), neurotrophin-3" glucagon, interleukins including IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, and IL-18, colony stimulating factors, lymphotoxin-p, tumour necrosis factor (TNF), leukemia inhibitory factor, oncostatin-M, and various ligands for cell surface molecules ELK and Hek (such as the ligands for eph-related kinases or LERKS).

Further proteins that can be produced using the processes and media of the invention include proteins comprising all or part of the amino acid sequence of a receptor for any of the above-mentioned proteins, an antagonist to such a receptor of any of the above-mentioned proteins, and proteins substantially similar to such receptors or antagonists.

Also, proteins that can be produced using the methods and media of the invention include proteins comprising all or part of the amino acid sequences of differentiation antigens (referred to as CD proteins) or their ligands or proteins substantially similar to either of these. Examples of such antigens are differentiation antigens including CD20, CD22, CD27, CD30, CD39, CD40, and ligands thereto.

Enzymatically active proteins or their ligands can also be produced using the processes and media of the invention. Examples include proteins comprising all or part of one of the following proteins, or their ligands, or proteins substantially similar to one of these: metalloproteinase-disintegrin family members, kinases, glucocerebrosidase, superoxide dismutase, tissue plasminogen activator, Factor VIII, Factor IX, apolipoprotein E, apolipoprotein A-1, globins, an IL-2 antagonist, alpha-1 antitrypsin, TNF-alpha Converting Enzyme, ligands for any of the above-mentioned enzymes, and numerous other enzymes and their ligands.

The methods and media of the invention can also be used to produce chimeric proteins selected in vitro to bind to a specific target protein and modify its activity, and antibodies or portions thereof and chimeric antibodies, i.e. antibodies having human constant antibody immunoglobulin domains coupled to one or more murine variable antibody immunoglobulin domain, fragments thereof, or substantially similar proteins. The processes of the invention may also be used to produce conjugates comprising an antibody and a cytotoxic or luminescent substance. Examples of antibodies, in vitro-selected chimeric proteins, or antibody/cytotoxin or antibody/luminophore conjugates that can be produced using the methods and media of the invention include those that recognise any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-ß, and analogues thereof, VEGF, TGF, TGF-ß2, TGF-p1, EGF receptor VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1,2,3, and 4, RANK, a RANK ligand, TNF-α, the adhesion molecule VAP-1, epithelial cell adhesion molecule (EpCAM), intercellular adhesion molecule-3 (ICAM-3), leukointegri-nadhesin, the platelet glycoprotein gpIIb/IIIa, cardiac myosin heavy chain, parathyroid hormone, MHC I, carcinoembryonic antigen (CEA), alpha-fetoprotein (AFP), tumour necrosis factor (TNF), Fc-y-1 receptor, HLA-DR 10 beta, HLA-DR antigen, L-selectin, and IFN-γ.

Naturally, the present invention extents in a further aspect of the present invention to a polypeptide obtainable by the process of the invention. In a preferred embodiment, the polypeptide comprises less than 30%, 25%, 20%, 18%, 17%, 16%, 15%, 14%, 13%, 12%, 11%, 10%, 9%, 8%, 7%, 6%, 5%, 4%, 3%, 2.5% and/or 2% C-terminal alpha amindated proline, preferably compared to a the same polypeptide expressed in a reference medium as outlined above or in the Examples. In particularly preferred embodiment, the polypeptide comprises less than 5% C-terminal alpha amindated proline.

The processes and media of the invention can also be used to produce recombinant fusion proteins comprising any of the above-mentioned biomolecules such as proteins or substantially similar proteins. For example, recombinant fusion proteins comprising one of the above-mentioned proteins plus a multimerisation domain, such as a leucine zipper, a coiled coil, an Fc portion of an antibody, or a substantially similar protein, can be produced using the methods and media of the invention. Specifically included among such recombinant fusion proteins are proteins in which at least a portion of TNFR or RANK is fused to an Fc portion of an antibody.

In another preferred embodiment, said process takes place in at least one bioreactor or culture vessel comprises:
shakeflasks
T-flasks
bags
rollerbottles
bioreactors, and/or
spinnerflasks.

Preferably, said bioreactor or culture vessel can have a volume between 50 ml and 40,000 L. Examples for standard bioreactor or culture vessel sizes: 50 ml (e.g. shake flask or T-flask), 500 ml, 2 L, 5 L, 15 L, 100 L and 300 L (e.g. bioreactor or bags), and 1,000 L, 2,000 L, 5,000 L, 10,000 L, 25,000 l and 40,000 L (large bioreactors).

In another preferred embodiment, cultivation of cells is carried out in adherent culture, for instance in monolayer culture. According to yet another preferred embodiment, the cultivation of cells may also take place in suspension culture.

Continuous and discontinuous cell culture processes can be utilized according to the present invention. Other known reactor technologies, e.g., perfusion technologies or the like can be also utilized. Batch processes and fed-batch processes are particularly preferred embodiments.

In accordance with the above, the present invention provides for the first time the knowledge that selenium ions are capable to regulate or retard the action or activity of the PAM enzyme. Thus, the present invention naturally extends in another embodiment to the use of selenium or a salt thereof as an inhibitor for PAM enzyme. In addition, another object of the invention is to provide the use of zinc or a salt thereof as an activator for carboxypeptidase (CP).

The invention also provides kits for use in the cultivation of culture cells. Kits according to the present invention comprise one or more containers, wherein at least a first container contains the culture medium of the invention or at least selenium, zinc and/or copper. Additional kits of the invention comprise one or more containers, wherein a first container contains a basal culture medium and a second container contains one or more essential trace elements as defined above, preferably in increased concentrations, i.e. concentrated form. Preferably, the solutions comprising ingredients are more concentrated than the concentration of the same ingredients in a 1× media formulation. The ingredients can be 10-fold more concentrated (10× formulation), 25-fold more concentrated (25× formulation), 50-fold more concentrated (50× formulation), or 100-fold more concentrated (100× formulation). Some or all of the ingredients as listed above, when admixed together in solution, can form a "basal culture medium." These kits may further comprise one or more additional containers containing one or more supplements such as cytokines, amino acids, vitamins, inorganic salts, sugars, buffering salts, lipids, insulins (or insulin substitutes) and/or transferrins (or transferrin substitutes, and/or animal peptides, and/or yeast peptides and plant peptides) or any combination thereof. The kit may comprise the medium in liquid or solid powder form or a combination of both. In addition, the kit may further comprise a batch of culture cells.

In accordance with the present invention, the medium or any of the above mentioned composition and/or solution may be liquid or solid powder, or a combination of both, a liquid solution comprising concentrated ingredients or a ready-to-use medium or composition. The powder can be generated by evaporating the water content of a 1×, 2×, 3×, 4×, 5×, 10×, 20×, 40×, 50× or 100× concentrated or x-fold more concentrated cell culture medium solution or composition. Alternatively, the medium ingredients are added in dry form in a suitable concentration, i.e. x-fold concentrated form as defined above, into a container.

The invention further provides a composition for use in growing cells, said composition comprising at least selenium in an effective amount as defined above. In a preferred embodiment, the composition further comprises zinc in an effective amount as defined above. Optionally, the composition may further comprise one or more cells, such as those described above. In a further preferred embodiment of the present invention, the composition comprises essentially consist of the medium as defined above.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto.

EXAMPLES

Additional details, features, characteristics and advantages of the object of the invention are disclosed in the subclaims, and the following description of the respective figures and examples, which, in an exemplary fashion and for illustration only, show preferred embodiments of the present invention. However, these figures and examples should by no means be understood as to limit the scope of the invention.

Detailed descriptions of conventional methods, such as those employed herein, can be found in the cited literature; see also "The Merck Manual of Diagnosis and Therapy" Seventeenth Ed. by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, $3^{rd}$ Ed. (Sambrook et al., Harbor Laboratory Press 2001); Short Protocols in Molecular Biology, $4^{th}$ Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, $3^{rd}$ Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. In addition, the disclosure content of the international applications PCT/EP2011/069756 or PCT/EP2013/057866, in particular the methods used in their respective experimental sections, are incorporated herein by reference.

Example 1: Effect of PAM Inhibitors on Amino Acid Amidation/Proline Amid Formation Experiments (using different illustrative glycoproteins) were performed in shake flask (SF) systems, where 500 L SFs with a final volume of 125 ml were used. All experiments started by thawing of a research working cell bank (rWCB), such as CHO cell line DP-12 (CHO DP-12 clone #1934 [CHO DP-12, clone #1934 aIL8.92 NB 28605/14] (ATCC® CRL-12445™) producing recombinant human anti-IL-8 or CHO-SSF cells expressing a monoclonal antibody directed to tumour necrosis factor, TNF (see PCT/EP2011/074181 for further details) followed by several subcultivations under standard conditions according to manufacture instructions until enough cells for the inoculation were available For all experiments, a 14 days generic fed batch fermentation was used and a generic feeding regime comprising feeding of glucose, glutamine and amino acids was performed. All SFs were incubated in a shaker incubator (Kuhner, Switzerland) at the following conditions: temperature of 36.5° C., $CO_2$=10% and shaking speed 200 rpm. For all experiments the same in-house growth and production media were used which exhibit similar ingredients and a similar content of ingredients as the fermentation media described for example in the international application WO 2011/134920.

In order to assess the influence of trace elements, the concentration of selected trace elements was systematically varied according to the suggested values. All results were finally confirmed in a bioreactor (BR) system, where 5 L glass bioreactors were used.

In both the SF and BR system, the cell growth and cell viability were measured with the Vi-Cell XR analyzer (Beckman Coulter) using the trypan blue exclusion method for cell viability determination and automated cell counting for determination of the cell concentration. The monoclonal antibody content was determined by affinity liquid chromatography (ALC). A calibration curve was made by diluting the generic reference. The results obtained were corrected with the appropriate response factor for the difference in molar extinction coefficients of both monoclonal antibodies. The results were expressed in gram (g) of protein per liter (L) of harvest.

At the end of 14 days of BR and SF bioprocesses (i.e., on day 14), harvests were sampled to 50 ml centrifuge tubes. The culture was centrifuged (3,220 g, 15 min), sterile filtered (Millipore Steriflip, SCGP00525), and samples were purified from harvests with a single purification step using MabSelectSuRe affinity columns. Purification was done either using AKTA chromatography system with 1 ml HiTrap column (GE Healthcare, cat. no. 11-0034-93) or TECAN Freedom EVO pipetting station with 200 µl Robo-Columns (Atoll, cat. no. 01050408R).

To measure the amount of C-terminal α-amidated Pro and the amount of C-terminal Lys, Cation Exchange Chromatography (CEX) was performed according to the laboratory procedure. Main charged variants were designated as 0K, pseudo 1K (1+) and pseudo 2K (2+). The positive charge refers to the Lys or α-amidated Pro at the C-terminus of the heavy chain. Charged variants (Lys, α-amidated Pro) were differentiated by CP cleavage of C-terminal Lys followed by the same CEX analysis. Structures eluting before the main three variants were designated as AP (acidic peaks) and those eluting after them as BP (basic peaks).

Example 2: Evaluation of Individual Trace Elements Concentration

An experiment investigating variable concentrations of individual trace elements on C-terminal α-amidation was performed. To detect the trace elements having a major influence on PAM activity, six trace elements that are included in highly enriched platform media, were first tested using a MinRes IV screening design (Design Expert software). In the following, only these trace elements which exhibit a significant effect on C-terminal α-amidation are further discussed and outlined in detail below. Hence, the concentrations for the tested elements, i.e., selenium, zinc and copper are described in Table 1 below.

TABLE 1

Setup of MinRes IV design with trace elements

| Trace element | Minimum [µM] | Maximum [µM] |
|---|---|---|
| Sodium Selenite ($Na_2SeO_3$) | 0.017 | 0.173 |
| Zinc Chloride ($ZnCl_2$) | 2.204 | 22.012 |
| Copper Chloride ($CuCl_2 \cdot 2H_2O$) | 0.204 | 2.041 |

The experiment was performed in 500 ml SF with a final volume of 125 ml. After 14 days of fed batch bioprocess, harvests were collected, centrifuged, sterile filtered through a PES membrane and immediately subjected to a single step affinity chromatography (AC) purification and a subsequent analysis of C-terminal α-amidation by size exclusion chromatography (SEC). Design Expert version 7.1.3 (Stat-Ease, Inc., Minneapolis, USA) was used to build the response surface design and to perform the statistical analysis of the experimental results. A MinRes IV design was used to determine the influence of the tested trace elements on cell productivity, C-terminal α-amidation and C-terminal carboxypeptidation of the investigated monoclonal antibody. Analyzed design expert (Stat-Ease, Inc., Minneapolis, USA) responses included end of fed-batch titer, amount of C-terminal α-amidated Pro and amount of C-terminal Lys.

Example 3: Increased Concentration of Selenium and Zinc Increases the Gram (g) of Protein Per Liter (L) of Harvest The standardized effects of the tested trace elements on titer (gram per liter) were first displayed graphically on Pareto Chart where the main effects (tested elements) were selected by clicking on the effects that were obviously larger than the others. Effects that were above the Bonferroni limit were certainly significant and effects that were above the t-Value limit were possibly significant. Effects that were below the t-Value limit were not selected as they were not significant. After selecting significant effects, the ANOVA statistical program was employed to confirm that only statistically significant effects were included in the model. The media additives that showed the main effect on a certain response displayed P-values lower than 0.1.

Figure 1:
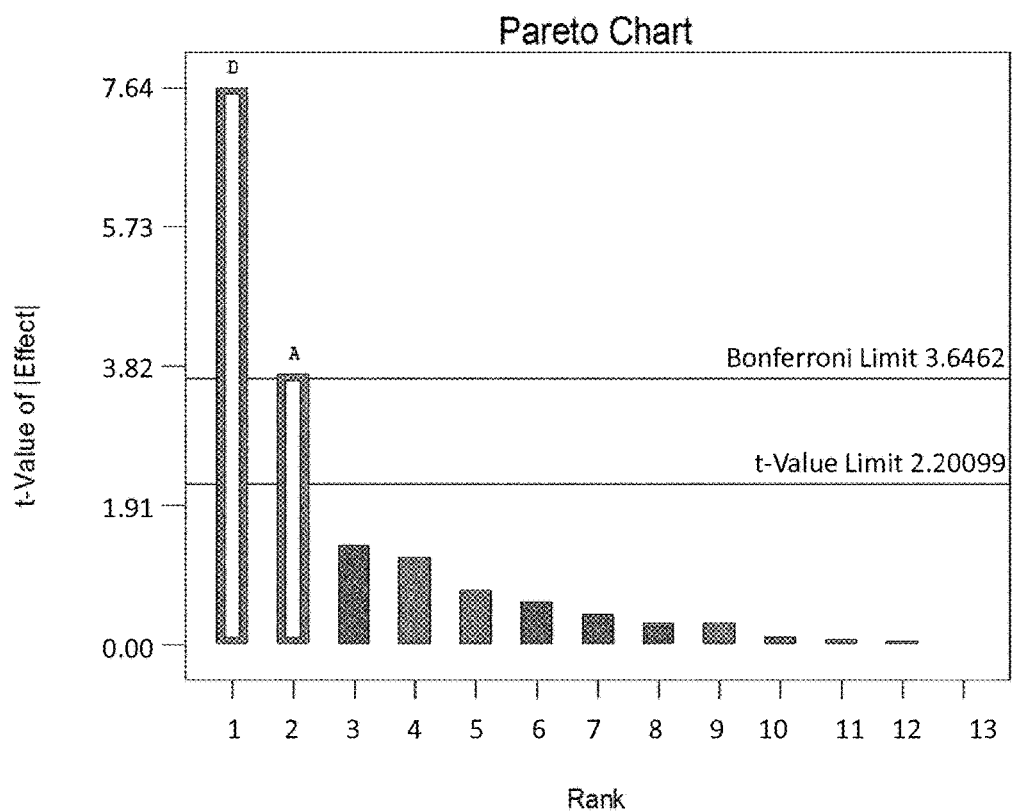
FIG. 1: Pareto chart created by design of experiment (DOE) for titer. Trace elements alone or in combination that had a significant effect on titer were ranked above Bonferroni limit and those that had a possible influence on titer were ranked above the t-Value limit. Trace elements that had no influence on titer were listed below the t-Value limit and were therefore not selected. A: sodium selenite (Na$_2$SeO$_3$), D: zinc chloride (ZnCl$_2$) in μm.
Figure 2:
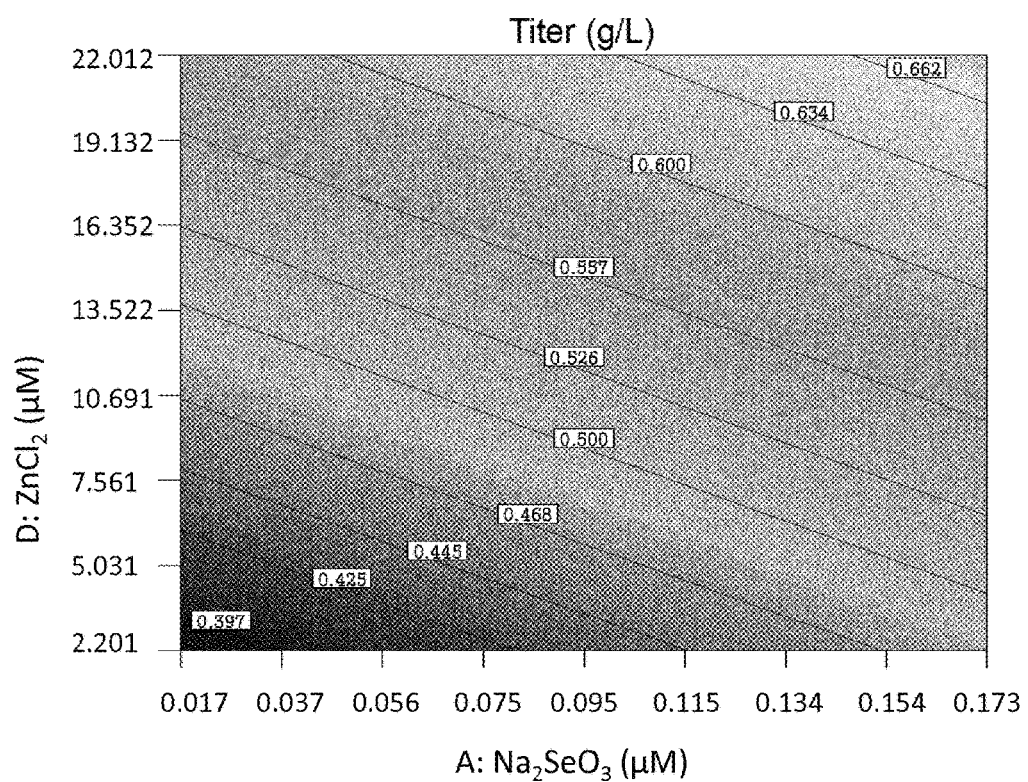
FIG. 2: Contour diagram created by DOE presenting the effect of zinc and selenium on titer. The bright colored zone on contour diagram represents the area of increased titer and the dark colored zone the area of decreased titer. The numbers in the white boxes represent the measured titers in g/L.

Among the factors (i.e. tested trace elements) having a major positive impact on titer, zinc and selenium were calculated to have a significant effect, and both trace elements were above the Bonferroni limit on the Pareto Chart. Both mentioned trace elements had an influence on titer also in combination since the interaction between the two of them was above the t-Value limit on the Pareto Chart (FIG. 1). By increasing the concentration of zinc from 2.201 μM to 22.012 μM and selenium from 0.017 μM to 0.173 μM in the production media, the titer was increased from 0.4 g/L up to 0.6 g/L or 0.5 mg/L, respectively. By increasing the concentration of zinc and selenium, the titer was increased from 0.4 g/L to above 0.65 g/L (FIG. 2).

Figure 3:
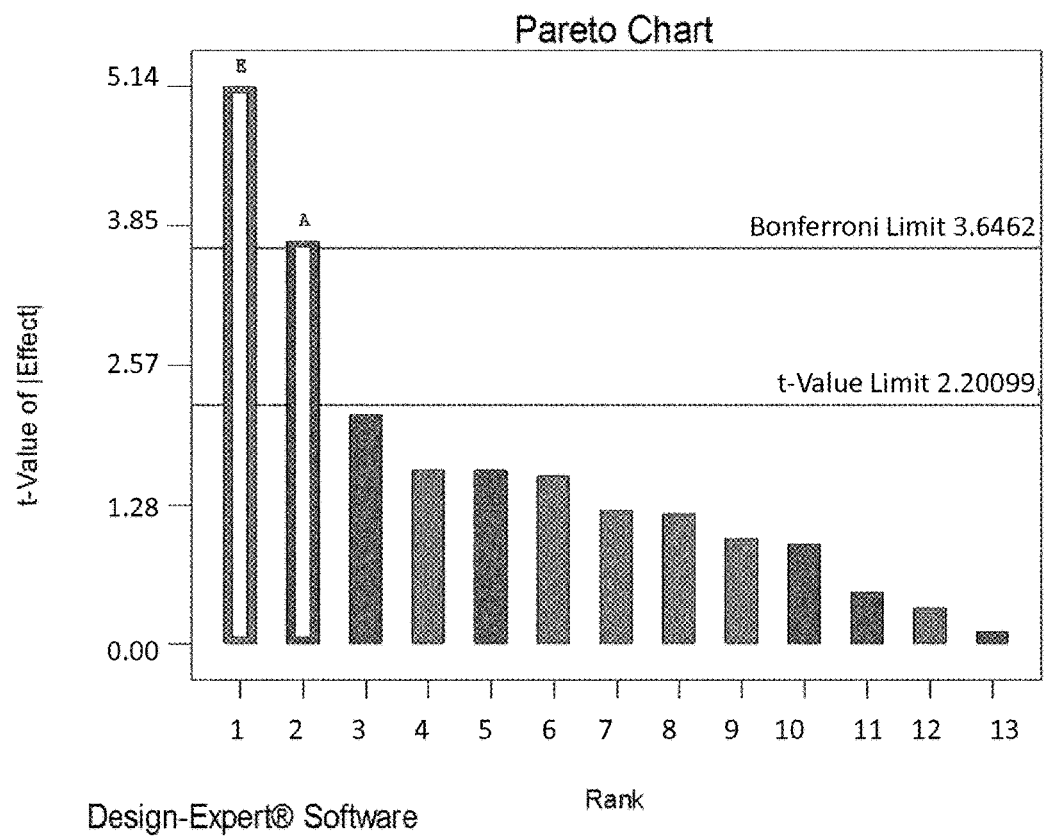
FIG. 3: Pareto chart created by DOE for the amount of C-terminal α-amidated Pro. Effects that were above the Bonferroni limit (E=copper chloride ($CuCL_2 \times 2H_2O$) and A=sodium selenite ($Na_2SeO_3$)) were certainly significant and effects that were above the t-Value limit were possibly significant. Effects that were below the t-Value limit were not selected as they were not significant.
Figure 4:
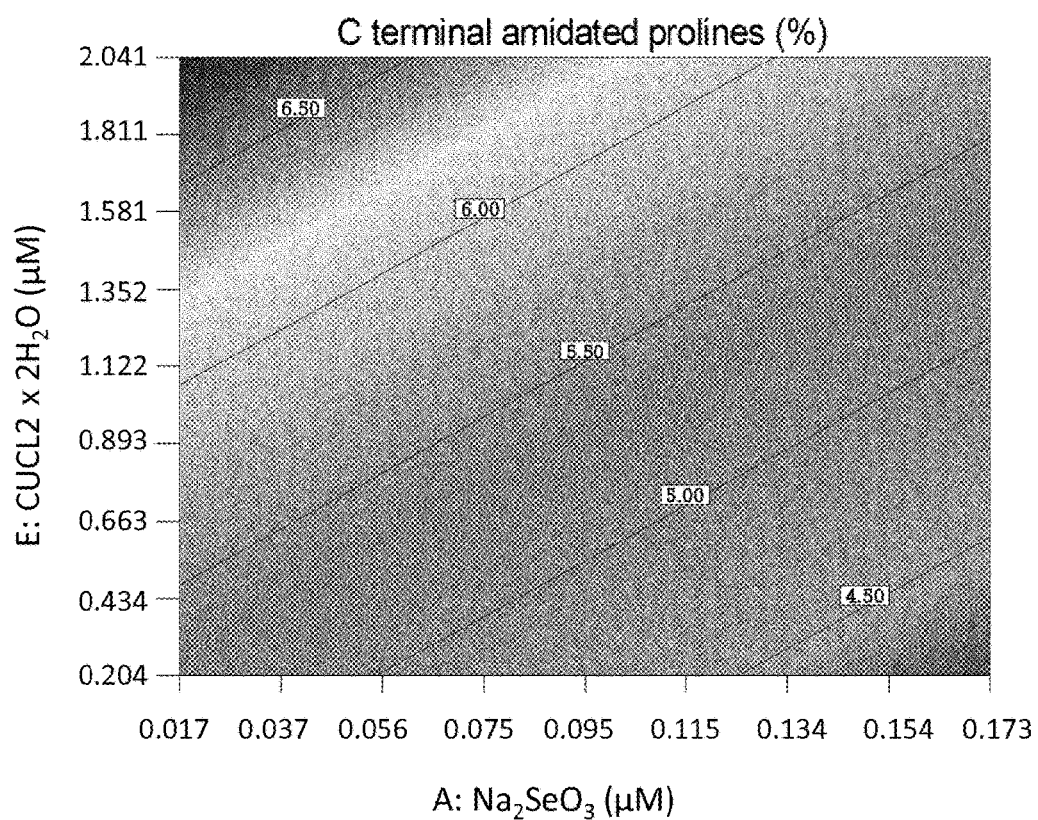
FIG. 4: Contour diagram created by DOE software where the effects of increased copper and selenium concentration on the amount of C-terminal α-amidated Pro (C-term. amidated Pro) is presented. An increased copper concentration in the media resulted in an increased PAM activity and an increased production of C-terminal α-amidated Pro. An increased selenium concentration resulted in a decreased PAM activity and a decreased production of C-terminal α-amidated Pro.

Example 4: Selenium (Se) and Copper (Cu) Influence C-terminal α-Amidated Pro When analyzing the effect of the tested trace elements on C-terminal α-amidation, it was expected that zinc and copper had the major influence and that those two factors would be far above the Bonferroni limit on a Pareto chart. As expected, a reduced concentration of copper showed a reduction of C-terminal α-amidation. Surprisingly, selenium in increased concentrations was shown to have a major reducing effect on C-terminal α-amidation (FIG. 3). A 10-fold increased concentration of selenium in the production media resulted in a decreased amount of C-terminal α-amidated Pro from 6.5% to 4.5%, and 10-fold increased concentration of copper resulted in an increased amount of C-terminal α-amidated Pro by 2.5% (FIG. 4).

From the obtained results it can be assumed that PAM activity can be efficiently regulated by varying the concentrations of copper and selenium in the production media. To decrease the C-terminal α-amidation, the concentration of selenium must be at the maximal (0.173 μM) and the concentration of copper at the minimal ranges (0.2 μM).

Example 5: Zinc (Zn) Exhibits Major Influence on the Presence of C-Terminal Lys Since zinc was excluded as a significant trace element for PAM regulation, the role of zinc on the percent (amount) of C-terminal Lys was examined. Lys is often the C-terminal amino acid and a substrate for the action of the enzyme CP. If the recombinant product has a C-terminal sequence of Pro-Gly-Lys, the Lys residue must be first cleaved off by the action of CP. The remaining terminal Gly is subsequently exposed to the action of the PAM enzyme which generates C-terminal amidated Pro in two sequential reactions (see above). Therefore, the amount of C-terminal α-amidation indirectly depends also on the action of CP.

Figure 5:
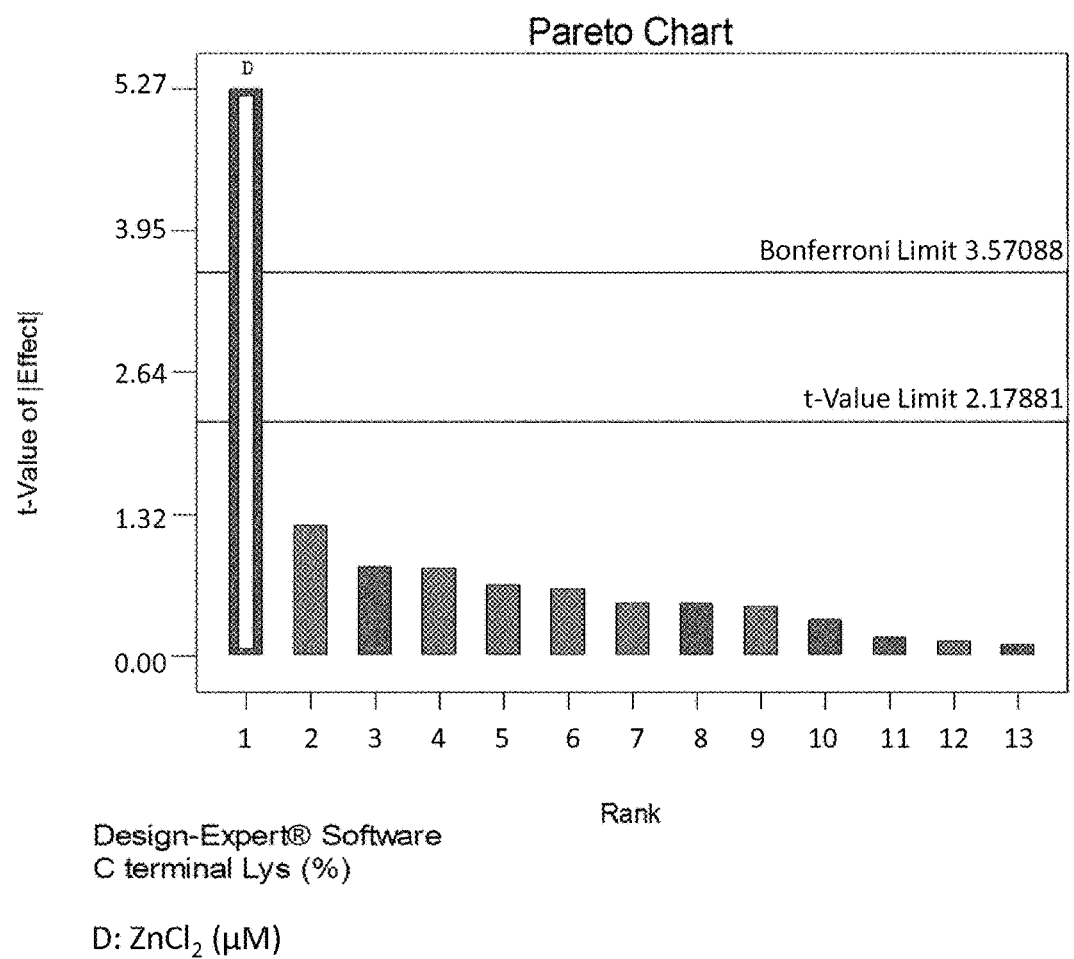
FIG. 5: Pareto charts created by DOE, presenting zinc as the factor with major influence on the amount of C-terminal Lys (C-term. Lys). Zinc was calculated to be the only factor with the t-Value above the Bonferroni limit.
Figure 6:
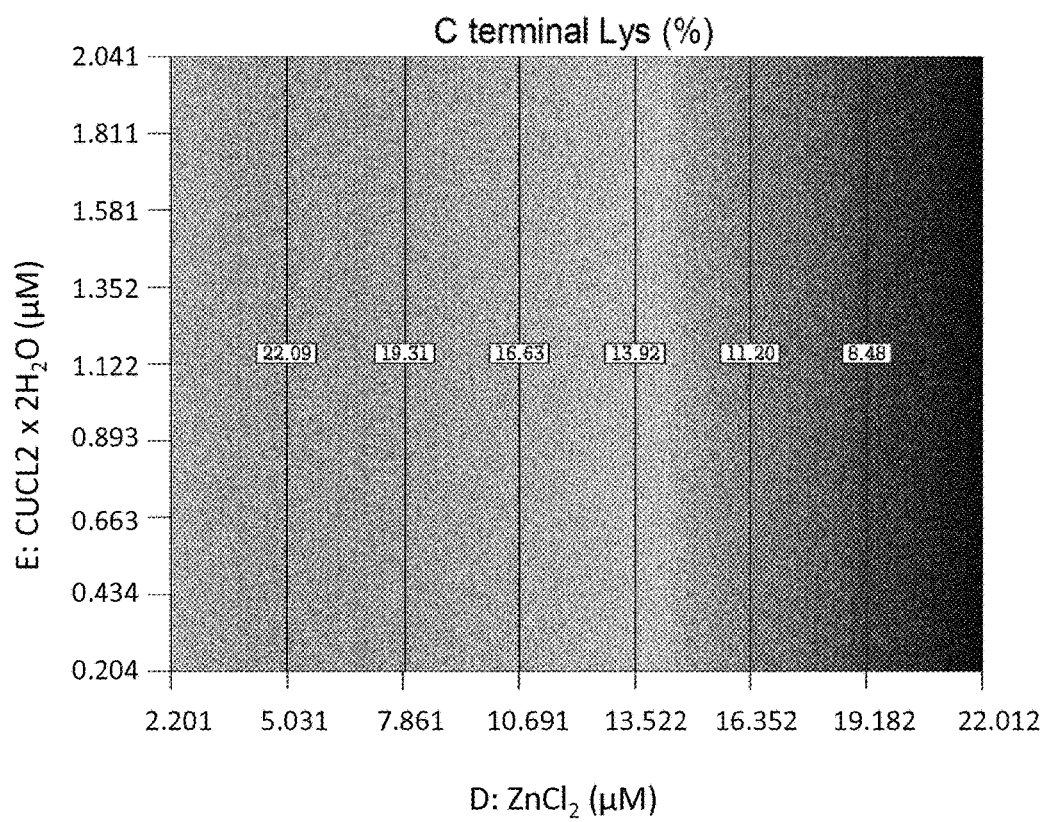
FIG. 6: Contour diagram created by DOE software where the effects of an increased zinc concentration on the amount of C-terminal Lys is presented. Increased zinc concentrations in media resulted in increased CP activity and consequently a decreased amount of C-terminal Lys.

When analyzing the effect of the tested trace elements on the amount of C-terminal Lys, only zinc was selected as the trace element with a major influence on the CP enzyme (FIG. 5). By a 10-fold increase of the zinc concentration, the amount of C-terminal Lys was decreased from 22% to 8.5% (FIG. 6), implying that zinc acts as an activator of CP.

Example 6: Evaluation of the Effective Concentrations of the Trace Elements Se, Zn and Cu After the screening experiment (i.e. experiment 1) with 6 trace elements, it was determined that zinc, selenium and copper had a main influence on the culture performance (titer), the C-terminal α-amidation and the C-terminal carboxypeptidation. In a follow-up experiment (i.e., experiment 2), the influence of concentration ranges of these three trace elements in the in-house medium was studied in a response surface central composite design.

Each of the selected trace elements was varied over 5 levels: plus and minus alpha (axial points), plus and minus 1 (factorial points) and central points. Therefore, a response surface central composite design was created, where zinc, copper and selenium concentrations were varied between 0.15 μM to 15 μM, 0.01 μM to 0.2 μM and 0.1 μM to 6 μM, respectively. The selected tested concentrations are presented in Table 2.

The experiment was performed in 500 ml SF with a final volume of 125 ml. After 14 days of fed batch bioprocess, harvests were collected, centrifuged, sterile filtered through a PES membrane and immediately subjected to a single step AC purification and a subsequent analysis of C-terminal α-amidation by SEC.

TABLE 2

Control Set points for experiment 2

| | Zinc Chloride (μM) | Copper Chloride (μM) | Sodium Selenite (μM) |
|---|---|---|---|
| SF01 | 7.41 | 0.18 | 2.98 |
| SF02 | 3.09 | 0.14 | 4.65 |
| SF03 | 7.41 | 0.10 | 2.98 |
| SF04 | 11.73 | 0.05 | 4.65 |
| SF05 | 3.09 | 0.14 | 1.31 |
| SF06 | 11.73 | 0.05 | 1.31 |
| SF07 | 7.41 | 0.10 | 2.98 |
| SF08 | 11.73 | 0.14 | 4.65 |
| SF09 | 7.41 | 0.02 | 2.98 |
| SF10 | 7.41 | 0.10 | 5.78 |
| SF11 | 11.73 | 0.14 | 1.31 |
| SF12 | 7.41 | 0.10 | 2.98 |
| SF13 | 7.41 | 0.10 | 2.98 |
| SF14 | 14.67 | 0.10 | 2.98 |
| SF15 | 7.41 | 0.10 | 2.98 |
| SF16 | 7.41 | 0.10 | 0.17 |
| SF17 | 3.09 | 0.05 | 4.65 |
| SF18 | 7.41 | 0.10 | 2.98 |
| SF19 | 0.15 | 0.10 | 2.98 |
| SF20 | 3.09 | 0.05 | 1.31 |

After performing the above described analytical steps, the measured values were inserted into the DOE program and analyzed. The α-value of statistical significance was set to 0.100, which means that factors with a P-value higher than 0.100 were excluded from the statistical mode since they were non-significant.

Figure 7:
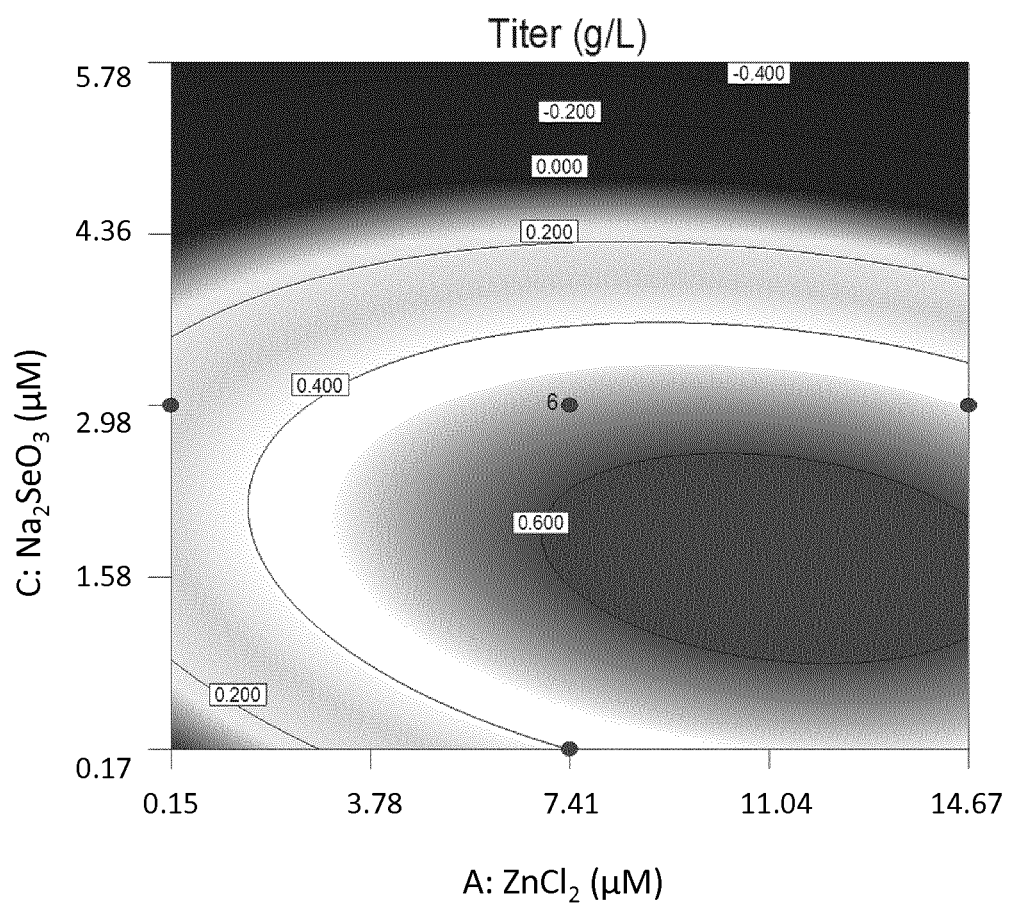
FIG. 7: Contour diagram created by DOE software where the effects of zinc and selenium on titer are presented. Increased zinc concentrations in media resulted in increased titers. A selenium concentration above 3 µM was shown to be toxic, leading to a titer reduction.

Example 7: Increased Concentration of Se and Zn Increases the Gram (g) of Protein Per Liter (L) of Harvest For the titer, a significant quadratic model was calculated with a p value of <0.0001. Only two tested trace elements were calculated to have a significant effect on titer: zinc with a P-value of 0.0029 and selenium with the P-value of <0.0001. Not significant lack of fit test was calculated (P-value of 0.1506) and "predicted R-squares" (0.8251) were in reasonable agreement with "Adj R-squares" (0.9283). A high "AdeqPrecisior" of 18.856 was calculated, meaning a high signal to noise ratio. The model was therefore appropriate to navigate the design space. The model suggested that the titer can be increased from 0.4 g/L to above 0.6 g/L by increasing the zinc concentration from 7 μM to 12 μM (FIG. 7). With regard to selenium, it could be shown in experiment 1 of Example 1 to 5, that it is possible to increase the titer by increasing the selenium concentration by a factor of 10 (FIG. 2). It is known that in fermentation media a usual selenium concentration is in the range of about 0.01-0.06 µM. In experiment 2 in Example 6 even higher selenium concentrations were tested. At the concentration of 3 µM, selenium became toxic to the cell culture and the viability dropped below 80% (data not shown). Consequently, the negative effect of a selenium concentration above 3 µM resulted in a titer decrease (FIG. 7). Therefore, the concentration of selenium must be kept at sub-toxic concentrations.

Example 8: Decreased Cu Concentration in Combination With Increased Se Concentration Drastically Decreases C-Terminal α-Amidated Pro For C-terminal α-amidation, a significant quadratic model was calculated with a P-value of 0.0001. All three tested factors (Zn, Cu and Se) were calculated to have a significant effect on the amount of C-terminal α-amidated Pro, zinc with the P-value of 0.0177, copper with the P-value of <0.0001 and selenium with the P-value of 0.0002. Not significant lack of fit test was calculated (P-value of 0.3239), which suggested that models can be used as a prediction tool. A high "AdeqPrecisior" of 20.363 was calculated, meaning a high signal to noise ratio. The model was therefore appropriate to navigate the design space. The model suggested that the C-terminal α-amidation can be significantly decreased by decreasing the concentration of copper. By decreasing the concentration of copper from 0.18 µM to 0.06 µM the amount of C-terminal α-amidated Pro slightly decreased from 2.2% to 2.1%.

Figure 8:
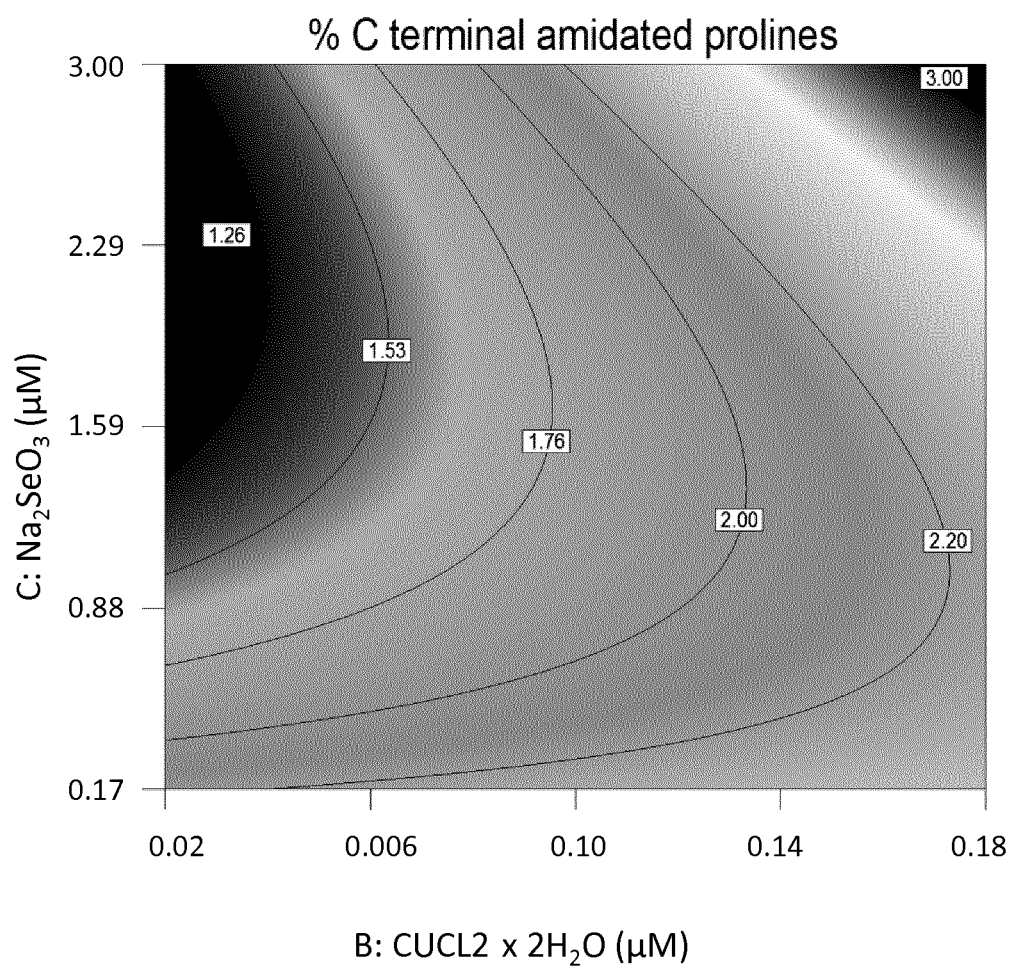
FIG. 8: Contour diagram created by DOE software where the effects of copper and selenium on the amount of C-terminal α-amidated Pro is presented. Increased selenium concentrations and decreased copper concentrations in media resulted in a decreased amount of C-terminal α-amidated Pro, indicating an inhibitory effect of selenium on the PAM enzyme.

Surprisingly, a significant negative effect of selenium on the PAM enzyme activity was shown as well. By increasing the concentration of selenium from 0.17 µM to 3.00 µM the amount of C-terminal α-amidated Pro decreased from 2.2% to 1.26% (FIG. 8).

In sum, it could be shown that in order to decrease the amount of C-terminal α-amidated Pro below 1%, the concentration of copper needs to be lowered and the concentration of selenium needs to be increased.

Example 9: Increased Zn Concentrations Decrease the Amount of C-Terminal Lys The significant importance of zinc as a cofactor regulating CP activity was also detected in experiment 2 in Examples 6 to 8, when analyzing the effect of the tested trace elements on the amount of C-terminal Lys. For CP activity, a significant quadratic model was calculated with a P-value of <0.0001. Zinc (P-value of <0.0001) was calculated as the major factor affecting the amount of C-terminal Lys. Some effect of copper (P-value of 0.0080) and selenium (P-value of 0.0014) on the activity of CP was also calculated. Not significant lack of fit test was calculated (P-value of 0.2830) and "predicted R-squares" (0.9663) were in reasonable agreement with "Adj R-squares" (0.9977). This suggested that models can be used as a prediction tool. A high "AdeqPrecisior" of 100.942 was calculated, meaning a high signal to noise ratio. The model was therefore appropriate to navigate the design space. The model suggested that by increasing the concentration of zinc from 0.15 µM to 5.00 µM the amount of C-terminal Lys was decreased from 15% to 5% (FIG. 9), meaning that zinc can act as the main activator of CP.

Example 10: Minimizing the Amount of C-Terminal Amidated Pro and Maximizing the Amount of C-Terminal Lys After analyzing experiment 2 in Examples 2 to 9, numerical and graphical optimization was performed using the DOE software.

First, the model for minimizing the amount of C-terminal amidated Pro was studied. The program calculated with high desirability (0.882) that, by using 0.4 µM copper and 2.3 µM selenium, there is a 95% probability that the amount of C-terminal amidated Pro will be within the prediction interval of 0.78% and 1.52%.

In the second optimization procedure, the model for maximizing the amount of C-terminal Lys was studied. The program calculated with high desirability (0.920) that by using 3.67 µM zinc, 2.3 µM selenium and 0.18 µM copper, there is a 95% probability that the amount of C-terminal Lys will be within the prediction interval of 12.27% and 13.02%.

Figure 10:
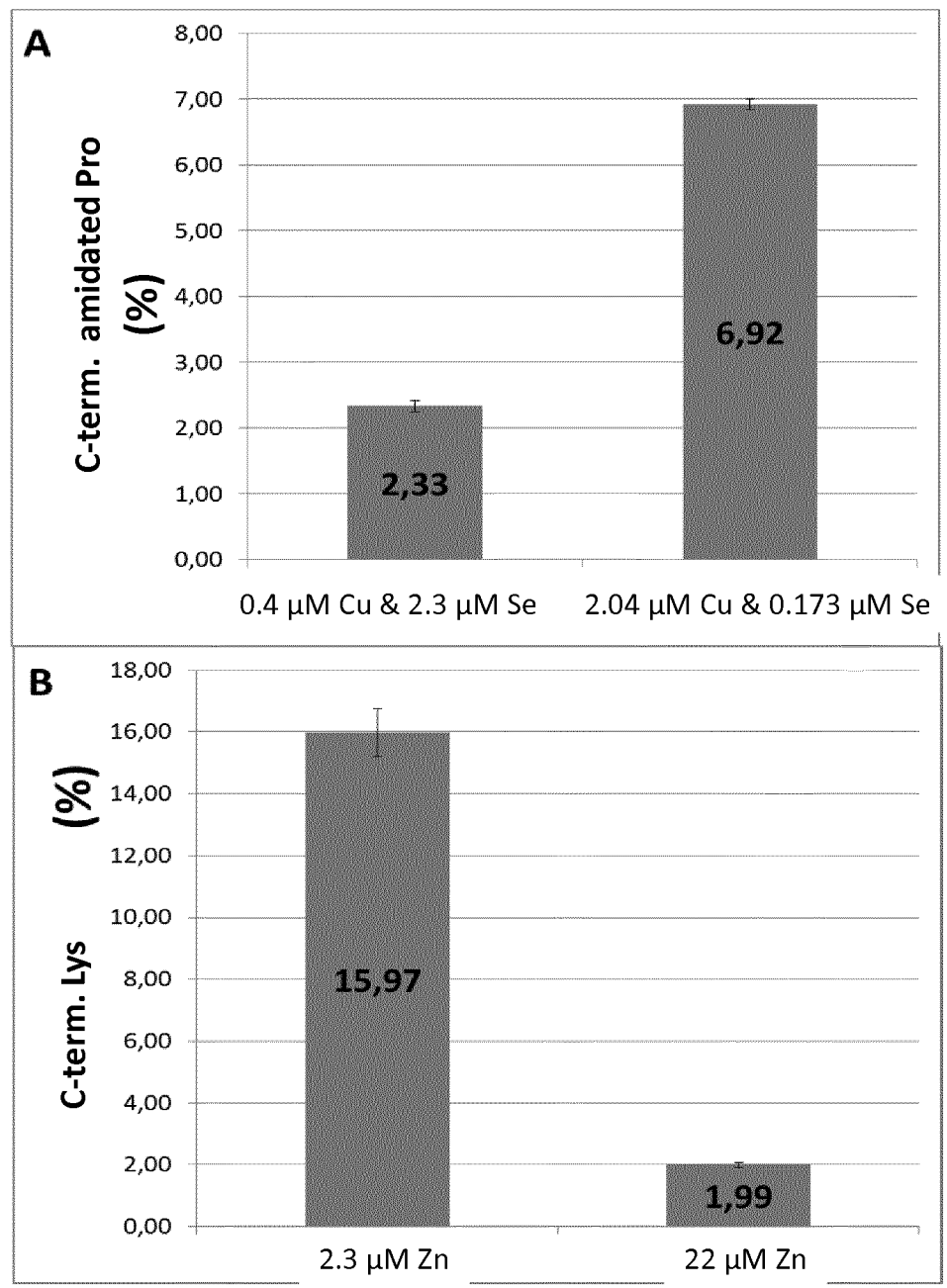
FIG. 10: Confirmation experiment performed in a SF system. A) The effect of a decreased copper and increased selenium concentration on the PAM activity (presented as amount of C-terminal α-amidated Pro) and comparison to the unchanged in-house medium comprising 2.04 µM copper (Cu) and 0.173 µM selenium (Se). B) The effect of decreased zinc concentration on the CP activity (presented as amount of C-terminal Lys) and comparison to the unchanged in-house medium comprising 22 µM zinc (Zn).

Therefore, two new media recipes were generated. In line with the calculated concentrations of copper (0.4 µM) and of selenium (2.3 µM), a fermentation medium with a decreased copper concentration and increased selenium concentration (as compared with the customized in-house media) was tested in three parallels using the SF system. In all SF approaches the same operational parameters as in the previous experiments were used. The measured amount of C-terminal α-amidated Pro in the medium with decreased copper and increased selenium concentration was 2.33%±0.09% and therefore slightly above the predicted interval. When comparing those results with the results measured with the respective protein produced in our in-house medium (2.04 µM copper and 0.173 µM selenium) the amount of C-terminal α-amidated Pro was significantly reduced (FIG. 10A).

For optimizing (i.e. reducing) the CP activity, a medium with reduced zinc concentration was designed, tested in three parallels, and compared to the unchanged in-house medium. By using medium comprising 2.3 µM zinc, the activity of CP was lowered and, accordingly, the amount of C-terminal Lys was increased from 1.99%±0.08% to 15.97%±0.79% (FIG. 10B).

Example 11: In Vivo Data Revealing Selenium as a Novel PAM Inhibitor

From the above described DOE experiments, it was concluded that the process of C-terminal α-amidation is tightly regulated by certain trace elements present in the medium during the fermentation process. In case of peptides ending with the amino acid sequence Pro-Gly-Lys the action of the two enzymes is needed, namely PAM and CP. In the previous experiments it could be shown that the activity of the PAM enzyme is not only regulated by the well-known cofactors zinc and copper. Surprisingly, it was also found that the presence of selenium in the medium significantly decreases the PAM enzyme's activity. The importance of zinc for the activity of the CP enzyme could also be shown.

The obtained SF results were finally also tested in a bioreactor (BR) environment. All experiments were performed in 5 L BRs.

Figure 12:
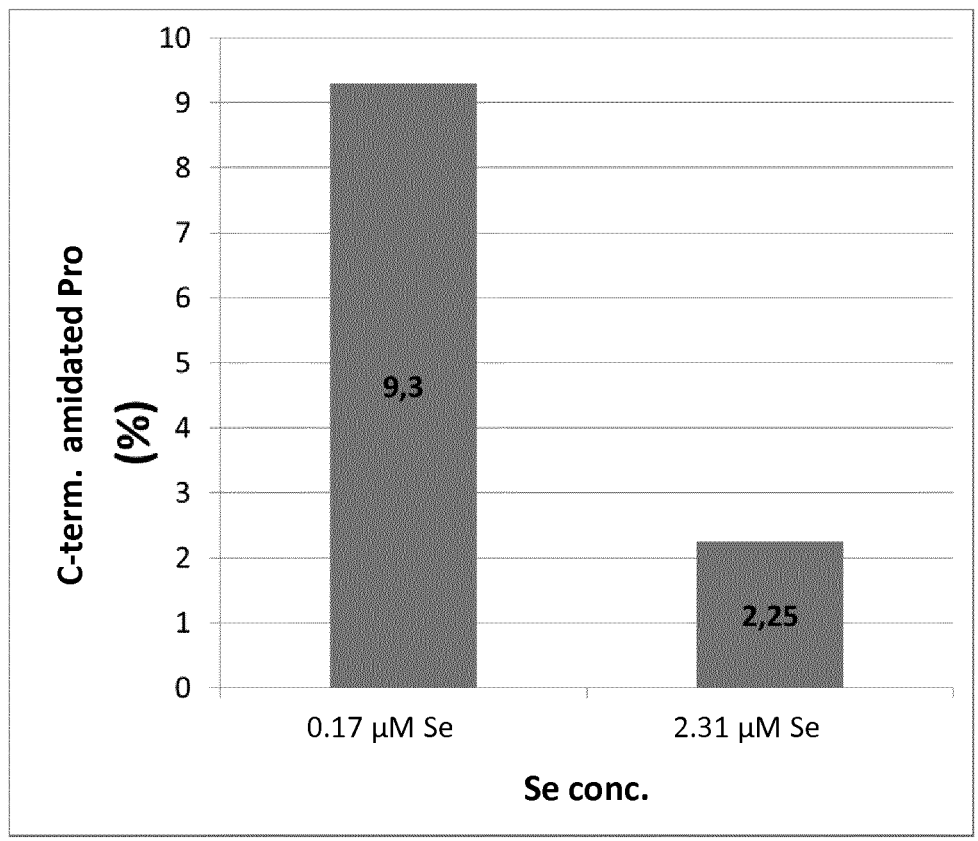
FIG. 12: The effect of an increased selenium concentration on in vivo PAM enzyme activity. By increasing the selenium concentration in the medium, the PAM activity was reduced which resulted in a drastically decreased amount of C-terminal α-amidated Pro.

To test the effect of selenium on the PAM activity, two media compositions were tested, namely a medium with 0.17 µM selenium and a medium with 2.31 µM selenium. The cell culture growth was well comparable between the two media and no significant decrease of viability was detected indicating that the increased selenium concentration was not toxic to the cells (FIG. 11A). With the increased selenium concentration the titer was decreased by 1 g/L (FIG. 11B) meaning that the tested selenium concentration resulted in a reduced but still acceptable productivity. The increased selenium concentration had a major influence on the amount of C-terminal α-amidated Pro. When producing recombinant proteins in media comprising 0.17 µM selenium, the resulting peptides comprised 9.3% C-terminal α-amidated Pro, whereas in the case of media comprising 2.31 μM selenium the corresponding amount was only 2.25% (FIG. 12).

The obtained results proved that selenium is a new inhibitory factor for PAM enzyme activity. Therefore, the action of the PAM enzyme and subsequently the amount of C-terminal α-amidated Pro—can be significantly regulated in vivo (even during protein production at large scale) by the concentration of available selenium in the fermentation medium.

Figure 13:
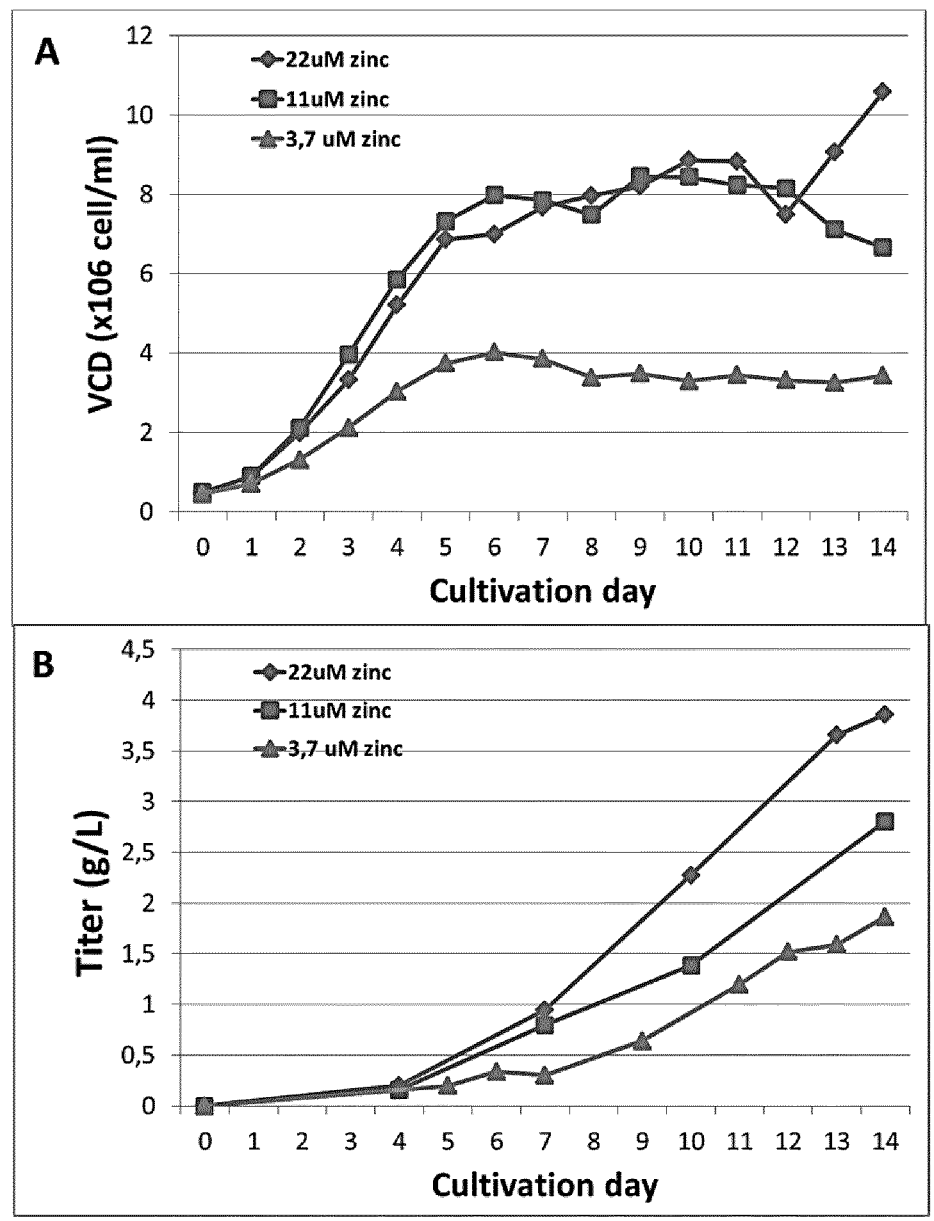
FIG. 13: Confirmation experiment performed in a BR system. The effect of a decreased zinc concentration (conc.) on the cell growth (A) and productivity (B) is depicted.

To test the effect of zinc on the CP activity, three different zinc chloride concentrations were tested, namely 3.7 μM, 11 μM and 22 μM. The cell culture growth was well comparable between the media comprising 22 μM and 11 μM zinc concentration, while a significantly lower growth was measured in the medium comprising 3.7 μM zinc (FIG. 13A) indicating a growth limitation due to an insufficient provision of zinc to the cells. In regard to productivity, a constant drop of productivity was measured with the decrease of the zinc concentration. In the media with the highest zinc concentration, a titer of 3.86 g/L was achieved, in the media with the zinc concentration of 11 μM the final titer was 2.90 g/L and in the media with the lowest zinc concentration the final titer was only 1.86 g/L (FIG. 13B).

Figure 14:
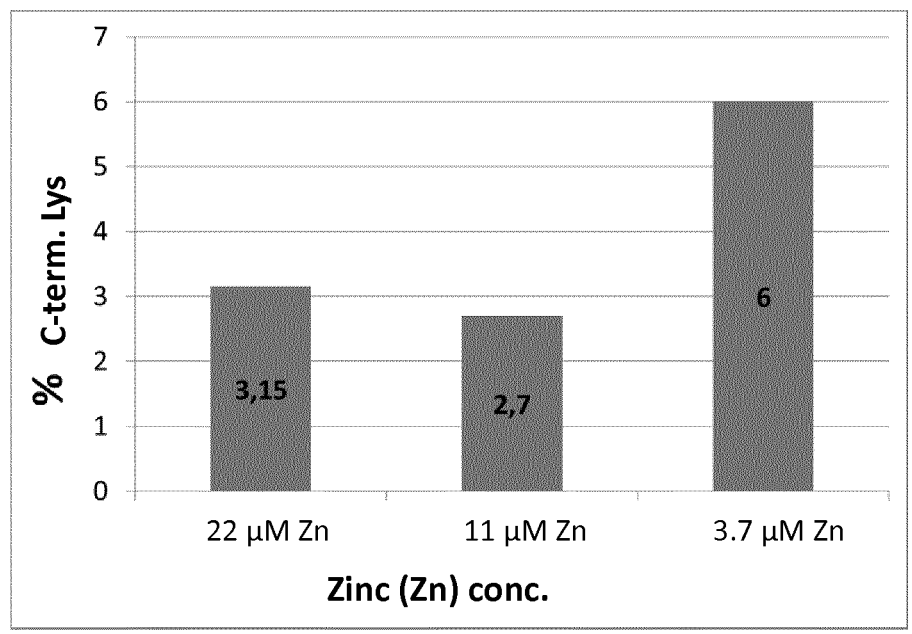
FIG. 14: The effect of a decreased zinc concentration on in vivo CP enzyme activity. By decreasing the zinc concentration (Zn conc.) in the medium the CP activity was reduced which resulted in a drastically increased amount of C-terminal Lys.

A significant effect of the increasing zinc concentration on the amount of C-terminal Lys was measured. When producing recombinant proteins in media comprising 22 μM zinc, the resulting peptides had only 3.15% of C-terminal Lys and in the media comprising 3.7 μM zinc, the content of C-terminal Lys was 6% (FIG. 14).

The obtained results proved that zinc is an activator of the CP enzyme. By increasing the zinc concentration, the CP enzyme was more active and resulted in a decreased amount of C-terminal Lys. Conversely, the amount of C-terminal Lys can be increased by decreasing the concentration of available zinc ions in the medium. And in turn, an increased amount of C-terminal Lys (indirectly) results in a decreased amount of C-terminal α-amidated Pro.

REFERENCES

Bradbury A F, Mistry J, Roos B A, Smyth D G. (1989). 4-Phenyl-3-butenoic acid, an in vivo inhibitor of peptidylglycine hydroxylase (peptide amidating enzyme). European Journal of Biochemistry; 189: 363-368.

Castigliore R, Gozzini L, Visco C, Galantino M. (1990) Use of PAM enzyme in solid phase peptide synthesis. United Kingdom Patent Application GB 2 220 938 A.

Eipper B A, Perkins S N, Husten E J, Johnson R C, Keutmann H T, Mains R E. (1991) Peptidyl-alpha-hydroxyglycine alpha-amidatinglyase: Purification, characterization, and expression. The Journal of Biological Chemistry. 266: 7827-7833.

Gozzini l. Peergo R, Castigliore R. (1991) Cofactors for enzymatic amidation. United Kingdom Patent Application GB 2 233 978A.

Gunther K. (1990) Cofactor for the PAM enzyme. European Patent Application EP 0 409 294 A1.

Kim K H, Seong B L. (2001) Peptide Amidation: Production of Peptide Hormones in vivo and in vitro. Biotechnology and Bioprocess Engineering; 6: 244-251.

Liu H, Gaza-Bulseco G, Faldu D, Chumsae C, Sun J. Heterogeneity of Monoclonal Antibodies. Journal of Pharmaceutical Sciences; 97: 2426-2447.

Maillère B, Mourier G, Herve M, Ménez A. (1995) Fine chemical modifications at N- and C-termini enhance peptide presentation to T cells by increasing the lifespan of both free and MHC-complexed peptides. Molecular Immunology; 32:1377-1385.

Merkler D J. (1994) C-terminal amidated peptides: production by the in vitro enzymatic amidation of glycine-extended peptides and the importance of the amide to bioactivity. Enzyme and Microbial Technology; 16: 450-456.

Metha N M, Carpenter S E, Consalvo A P. (2009) C Terimanl α-Amidation. In: Walsh G. Post translational modification of Protein biopharmacetuticals. Wiley-VCH Verlag GmbH, Co.KGaA, Weinheim, Germany, pp. 253-276.

The invention claimed is:

1. A cell culture medium for controlling a-amidation and C-terminal cleavage of an amino acid residue of at least one polypeptide produced in a cell culture, wherein the medium or a compound in the medium comprises trace elements zinc and selenium, wherein zinc is in a concentration ranging from 0.2 μM to 20 μM and activates carboxypeptidase and selenium is in a concentration ranging from 1 μM to 2.4 μM and inhibits peptidylglycine α-amidating monooxygenase (PAM) enzyme.

2. The medium of claim 1, wherein the trace elements
   i) decrease the amount of C-terminal α-amidated proline and/or increase the amount of C-terminal lysine; and
   ii) are in the forms of ions or salts thereof or are present in a compound in the form of ions or salts thereof.

3. The medium of claim 1, further comprising copper in a ranging from 0.02 μM to 1 μM.

4. The medium of claim 1, 2 or 3, wherein the medium further comprises zinc in a concentration ranging from 3 μM to 15 μM.

5. The medium of claim 2 or 3, wherein the amount of
   i) C-terminal α-amidated proline of the polypeptide produced is decreased using said medium compared to the use of a medium containing 2.04 μM copper and 0.173 μM selenium; and/or
   ii) C-terminal lysine of the polypeptide expressed is increased using said medium compared to the use of a medium containing 22 μM zinc.

6. The medium of claim 1, wherein said polypeptide is
   i) a heterologously expressed polypeptide, wherein the heterologous expression takes place in a eukaryotic cell-based expression system; and/or
   ii) selected from the group consisting of:
      a) an antibody, a fragment of said antibody or a derivative of said antibody;
      b) a fusion protein, and
      c) non-antibody proteins.

7. The medium of claim 6, wherein said eukaryotic cell-based expression system comprises a eukaryotic cell selected from the group consisting of an insect cell, a plant cell, an algae cell, a fungus cell, a mammalian cell and an animal cell.

8. The medium of claim 7, wherein said eukaryotic cell-based expression system is a mammalian expression system.

9. The medium of claim 8, wherein said mammalian expression system is at least one mammalian cell line selected from the group consisting of: a baby hamster kidney cells line, a Chinese hamster ovary cell line, a murine myeloma cell line, a human embryonic kidney cell line, a human retina-derived cell line and an amniocyte cell line.

* * * * *